(12) United States Patent
Lange et al.

(10) Patent No.: US 8,937,184 B2
(45) Date of Patent: Jan. 20, 2015

(54) 1H-IMIDAZOLE DERIVATIVES AS CANNABINOID CB2 RECEPTOR MODULATORS

(75) Inventors: Josephus H. M. Lange, Weesp (NL); Herman H. Van Stuivenberg, Weesp (NL); Bernard J. Van Vliet, Weesp (NL)

(73) Assignee: Abbvie B.V., Hoofddorp (NL)

( * ) Notice: Subject to any disclaimer, the term of this patent is extended or adjusted under 35 U.S.C. 154(b) by 572 days.

(21) Appl. No.: 11/353,155

(22) Filed: Feb. 14, 2006

(65) Prior Publication Data

US 2006/0194779 A1     Aug. 31, 2006

Related U.S. Application Data

(60) Provisional application No. 60/653,091, filed on Feb. 16, 2005.

(51) Int. Cl.
| | | |
|---|---|---|
| *C07D 233/90* | (2006.01) | |
| *C07D 403/04* | (2006.01) | |
| *C07D 403/06* | (2006.01) | |
| *C07D 417/04* | (2006.01) | |
| *C07D 417/06* | (2006.01) | |
| *C07D 403/02* | (2006.01) | |

(52) U.S. Cl.
CPC ..................... *C07D 403/02* (2013.01)
USPC ........ 548/333.5; 514/400; 514/314; 514/367; 514/397; 514/370; 514/341; 514/254.05; 514/217.09; 540/603; 544/370; 546/171; 546/274.7; 546/164; 546/274.1; 546/210; 546/112; 548/162; 548/311.7; 548/190

(58) Field of Classification Search
USPC ...................................................... 548/333.5
See application file for complete search history.

(56) References Cited

U.S. PATENT DOCUMENTS

| 4,596,598 | A | * | 6/1986 | Leone-Bay et al. | .......... | 504/279 |
| 4,740,513 | A | * | 4/1988 | Campbell et al. | ............. | 514/312 |
| 4,808,213 | A | * | 2/1989 | Schmierer et al. | ............ | 504/279 |
| 6,630,495 | B1 | * | 10/2003 | Cooke et al. | .................. | 514/357 |

FOREIGN PATENT DOCUMENTS

| WO | WO 01/58869 | A2 | | 8/2001 |
| WO | WO 03/007887 | A2 | | 1/2003 |
| WO | WO 03/027076 | A2 | | 4/2003 |
| WO | WO 03/040107 | A1 | | 5/2003 |
| WO | WO 03/063781 | A2 | | 8/2003 |
| WO | WO-2005/000821 | A1 | * | 1/2005 |
| WO | WO-2005/060665 | A2 | * | 7/2005 |
| WO | WO-2006/076202 | A1 | * | 7/2006 |
| WO | WO-2007/042544 | A2 | * | 4/2007 |
| WO | WO-2007/042546 | A1 | * | 4/2007 |

OTHER PUBLICATIONS

Akaji et al., "Efficient Coupling of α,α-Dimethyl Amino Acid using a New Chloro Imidazolidium Reagant, CIP," *Tetrahedron Letters* 35:3315-3318 (1994).
Albericio et al., "On the Use of PyAOP, a phosphonium salt derived from HOAt, in Solid-Phase Peptide Synthesis," *Tetrahedron Letters* 38:4853-4856 (1997).
Bickel, "The Pharmacology and Biochemistry of N-oxides," *Pharmacological Reviews* 21:325-355 (1969).
Dell'Erba et al., "Reactions of arylazosulfones with the conjugate bases of (*tert*-butoxycarbonyl) methyl and tosylmethyl isocyanide. Synthesis of substituted 1-arylimidazoles," *Tetrahedron* 52:2125-2136 (1997).
Gomez-Sanchez et al., "Studies on Nitroenamines. Part III.[1], Synthesis and Spectral Properties of 4-Acyl-1-arylimidazoles," *J. Heterocyclic Chem.* 24:1757-1763 (1987).
Gupta et al., "Ring-substituted imidazoles as a new class of antituberculosis agents," *Eur. J. Med. Chem.* 39:805-814 (2004).
Haberhauer and Rominger, "Synthesis of a new class of imidazole-based cyclic peptides," *Tetrahedron Letters* 43:6335-6338 (2002).
Hanus et al., "HU-308: A specific agonist for $CB_2$, a peripheral cannaboid receptor," *Proc. Natl. Acad. Sci. USA* 96:14228-14233 (1999).
Ibrahim et al., "Activation of $CB_2$ cannabinoid receptors by AM1241 inhibits experimental neuropathic pain: Pain inhibition by receptors not present in the CNS," *Proc. Natl. Acad. Sci. USA* 100:10529-10533 (2003).
Iwamura et al., "In Vitro and in Vivo Pharmacological Characterization of JTE-907, a Novel Selective Ligand for Cannabinoid $CB_2$ Receptor," *J. Pharmacol. Exp. Ther.* 296:420-425 (2001).
Klein et al., "The cannaboid system and immune modulation," *J. Leukoc. Biol.* 74:486-496 (2003).
Levin et al. "An altered procedure for the aluminium-mediated conversion of esters to amides," *Synth. Commun.*, 12: 989-993 (1982).
Lipshutz et al., "Single-flask polyfunctionalization of the imidazole ring; a streamlined route to the antitumor agent carmethizole," *Tetrahedron Letters* 33:5865-5868 (1992).

(Continued)

*Primary Examiner* — Laura L. Stockton
(74) *Attorney, Agent, or Firm* — Finnegan, Henderson, Farabow, Garrett & Dunner LLP

(57) ABSTRACT

The invention relates to a group of 1H-imidazole derivatives which are modulators of cannabinoid $CB_2$ receptors, to methods for the preparation of these compounds, to novel intermediates useful for the synthesis of said imidazole derivatives, to methods for the preparation of these intermediates, to pharmaceutical compositions containing one or more of these 1H-imidazole derivatives as active ingredient, as well as to the use of these pharmaceutical compositions for the treatment of disorders in which cannabinoid $CB_2$ receptors are involved.

The compounds have the general formula (I)

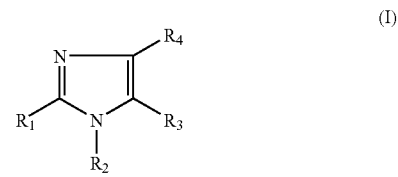

(I)

wherein $R_1$-$R_4$ have the meanings given in the specification.

8 Claims, No Drawings

(56) References Cited

OTHER PUBLICATIONS

Matsuura et al., "Synthesis of 1*H*-Imidazoles by the Simple Ring Transformation of 5-Acylaminouracils and 5-Acylaminopyrimidin-4(3*H*)-ones," *J. Chem. Soc. Perkin Trans.* I, 11:2821-2826 (1991).

Montalbetti et al., "Amide bond formation and peptide coupling," *Tetrahedron* 61:10827-10852 (2005).

Raitio et al., "Targeting the Cannabinoid CB2 Receptor: Mutations, Modeling and Development of CB2 Selective Ligands," *Curr. Med. Chem.* 12:1217-1237 (2005).

Shoemaker et al., "Agonist-Directed Trafficking of Response by Endocannabinoids Acting at CB2 Receptors," *J. Pharmacol. Exp. Ther.* 315:828-838 (2005).

Ueda et al., "A Novel Ring Transformation of 5-Acylaminouracils and 5-AcylaminoPyrimidin-4(3H)-ones Into Imidazoles," *Tetrahedron Letters* 29:4607-4610 (1988).

Van Berkel et al., "Base-free anaerobic Cu(II) catalysed aryl-nitrogen bond formations," *Tetrahedron Letters* 45:7659-7662 (2004).

Zhang et al., "Induction of CB2 receptor expression in the rat spinal cord of neuropathic but not inflammatory chronic pain models," *Eur. J. Neuroscience* 17:2750-2754 (2003).

Bell et al., "2(1*H*)-Quinolinones with Cardiac Stimulant Activity. 3. Synthesis and Biological Properties of 6-Imidazol-1-yl Derivatives," *J. Med. Chem*, 1989, 32, 1552-1558.

Lange et al., "Bioisosteric Replacements of the Pyrazole Moiety of Rimonabant: Synthesis, Biological Properties, and Molecular Modeling Investigations of Thiazoles, Triazoles, and Imidazoles as Potent and Selective $CB_1$ Cannabinoid Receptor Antagonists," *J. Med. Chem.* 2005, 48, pp. 1823-1838.

Lange et al., "Synthesis and SAR of novel imidazoles as potent and selective cannabinoid $CB_2$ receptor antagonists with high binding efficiencies," *Bioorganic & Medicinal Chemistry Letters* 20 (2010) pp. 1084-1089.

\* cited by examiner

1H-IMIDAZOLE DERIVATIVES AS CANNABINOID CB2 RECEPTOR MODULATORS

This application claims the benefit of U.S. provisional application No. 60/653,091, filed Feb. 16, 2005, the disclosure of which is incorporated herein by reference.

The present invention relates to a group of 1H-imidazole derivatives which are modulators of cannabinoid $CB_2$ receptors, to methods for the preparation of these compounds, to novel intermediates useful for the synthesis of said imidazole derivatives. The invention also relates to the use of a compound disclosed herein for the manufacture of a medicament giving a beneficial effect. A beneficial effect is disclosed herein or apparent to a person skilled in the art from the specification and general knowledge in the art. The invention also relates to the use of a compound of the invention for the manufacture of a medicament for treating or preventing a disease or condition. The invention also relates to a new use for the treatment of a disease or condition disclosed herein or apparent to a person skilled in the art from the specification and general knowledge in the art. In embodiments of the invention specific compounds disclosed herein are used for the manufacture of a medicament useful in the treatment of disorders in which cannabinoid $CB_2$ receptors are involved, or that can be treated via manipulation of those receptors.

1H-Imidazole derivatives as $CB_1$ receptor modulators are known from WO 03/027076, WO 03/063781, WO 03/040107 and WO 03/007887. (Morpholin-4-yl)alkyl-(1H)-imidazole derivatives have been claimed as $CB_2$ receptor modulators in WO 01/58869 disclosing three specific imidazoles (examples 64, 65 and 66). all containing an L-phenylalanine derived carboxamide group at the 4-position of their (1H)-imidazole moiety. 1-Aryl-(1H)-imidazole derivatives have been claimed in U.S. Pat. No. 4,952,698 as CNS active compounds. Recent advances in the field of $CB_2$ receptor selective ligands have been reviewed by K. H. Raitio et al. (Curr. Med. Chem. 2005, 12, 1217-1237).

Surprisingly, novel 1H-imidazole derivatives have been found which bind to the $CB_2$ receptor, including compounds having approximately hundred-fold higher $CB_2$ receptor affinities as compared to the prior art compounds which were exemplified in WO 01/58869. Moreover, many of the compounds within this invention are highly $CB_2$ receptor subtype selective which means that they bind with a much higher affinity to the $CB_2$ receptor than to the $CB_1$ receptor. The compounds within this invention are either $CB_2$ receptor agonists, $CB_2$ receptor partial agonists, $CB_2$ receptor antagonists or $CB_2$ receptor inverse agonists.

In one embodiment, the invention relates to compounds of formula (I)

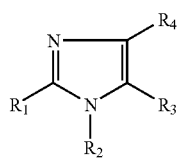

(I)

or a tautomer, a stereoisomer, or N-oxides thereof, or a pharmacologically acceptable salt, hydrate or solvate of any of the foregoing, wherein:

$R_1$ is chosen from: hydrogen; halogen; $C_{1-3}$-alkyl optionally substituted with at least one substituent chosen from 1-3 fluorine atoms, hydroxy, and amino; $C_{2-3}$-alkynyl or $C_{2-3}$-alkenyl, wherein the $C_{2-3}$-alkynyl and $C_{2-3}$-alkenyl are optionally substituted with 1-3 fluorine atoms; acetyl; cyclopropyl; cyano; methylsulfonyl; ethylsulfonyl; methylsulfinyl; ethylsulfinyl; trifluoromethylsulfanyl; methylsulfanyl; ethylsulfanyl; formyl; and $C_{2-4}$-heteroalkyl having at least one heteroatom chosen from nitrogen, oxygen, and sulfur, $R_2$ is chosen from:
  phenyl optionally substituted with 1, 2, 3, 4 or 5 substituents Y, wherein can be the same or different, and is chosen from methyl, ethyl, propyl, methoxy, ethoxy, hydroxy, chloro, iodo, bromo, fluoro, trifluoromethyl, trifluoromethoxy, methylsulfonyl, carbamoyl, phenyl and cyano;
  heteroaryl having at least one heteroatom chosen from nitrogen, oxygen, and sulfur, which is optionally substituted with 1, 2 or 3 substituents Y, as defined above, with the proviso that $R_2$ is not 6-methyl-2-pyridyl;
  mono-unsaturated and fully saturated 4-10 membered monocyclic, fused bicyclic and fused tricyclic carbocyclic ring systems;
  mono-unsaturated and fully saturated 4-10 membered monocyclic, fused bicyclic and fused tricyclic heterocyclic ring systems having at least one heteroatom chosen from nitrogen, oxygen, and sulfur, which carbocyclic and heterocyclic ring systems are optionally substituted with 1-5 substituents chosen from methyl, ethyl, amino, hydroxy, and fluoro;
  a group of formula $CH_2$—$R_5$, wherein $R_5$ is chosen from phenyl substituted with 1, 2, 3, 4 or 5 substituents Y as defined above; heteroaryl having at least one heteroatom chosen from nitrogen, oxygen, and sulfur, and 1,2,3,4-tetrahydronaphthyl, and indanyl, wherein the heteroaryl, 1,2,3,4-tetrahydronaphtyl, and indanyl are optionally substituted with 1, 2 or 3 substituents Y as defined above; mono-unsaturated and fully saturated monocyclic, fused bicyclic and fused tricyclic 4-10 membered carbocyclic ring systems; mono-unsaturated and fully saturated 4-10 membered monocyclic, fused bicyclic and fused tricyclic heterocyclic ring systems having at least one heteroatom chosen from nitrogen, oxygen, and sulfur, wherein the carbocyclic and heterocyclic ring systems are optionally substituted with 1-5 substituents chosen from methyl, ethyl, amino, hydroxy, and fluoro; and
  methylsulfonylaminoalkyl; methylsulfonylalkyl; and acetamidoalkyl, $R_3$ is chosen from: hydrogen; halogen; formyl; $C_{1-6}$-alkylsulfonyl; $C_{1-6}$-alkylsulfinyl; $C_{1-6}$-alkylsulfanyl; trifluoromethylsulfanyl; benzylsulfanyl; cyano; $C_{1-8}$-alkyl optionally substituted with 1-5 substituents chosen from fluoro, hydroxy, and amino; $C_{2-6}$-alkynyl, $C_{2-6}$-alkenyl, $C_{1-6}$-alkanoyl, $C_{3-8}$-cycloalkyl, $C_{5-8}$-heterocycloalkyl having at least one heteroatom chosen from nitrogen, oxygen, and sulfur, and $C_{2-6}$-heteroalkyl having at least one heteroatom chosen from nitrogen, oxygen, and sulfur, wherein the $C_{2-6}$-alkynyl, $C_{2-6}$-alkenyl, $C_{1-6}$alkanoyl, $C_{3-8}$-cycloalkyl, $C_{5-8}$-heterocycloalkyl, and $C_{2-6}$-heteroalkyl are optionally substituted with at least one substituent chosen from 1-3 methyl groups, ethyl, amino, hydroxy, and 1-3 fluorine atoms; phenyl optionally substituted with 1-5 substituents Y, as defined above; heteroaryl having at least one heteroatom chosen from nitrogen, oxygen, and sulfur optionally substituted with 1, 2 or 3 substituents Y, as defined above; benzyl and heteroarylmethyl having at least one heteroatom chosen from nitrogen, oxygen, and sulfur, wherein the benzyl and heteroarylmethyl are optionally substituted with 1, 2 or 3 substituents Y, as defined above, R₄ is chosen from formula (i) and formula (ii)

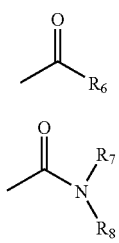

(i)

(ii)

wherein:

R₆ is chosen from: C$_{4-8}$ branched and linear alkyl, C$_{3-8}$ cycloalkyl, C$_{3-8}$-cycloalkyl-C$_{1-2}$-alkyl, C$_{5-7}$-heterocycloalkyl-C$_{1-2}$-alkyl having at least one heteroatom chosen from nitrogen, oxygen, and sulfur, C$_{5-10}$-bicycloalkyl, C$_{5-10}$-bicycloalkyl-C$_{1-2}$-alkyl, C$_{5-10}$-heterobicycloalkyl-C$_{1-2}$-alkyl having at least one heteroatom chosen from nitrogen, oxygen, and sulfur, C$_{6-10}$-tricycloalkyl, C$_{6-10}$-tricycloalkyl-C$_{1-2}$-alkyl, and C$_{6-10}$-heterotricycloalkyl-C$_{1-2}$-alkyl having at least one heteroatom chosen from nitrogen, oxygen, and sulfur, which groups are each optionally substituted with 1-5 substituents chosen from methyl, hydroxy, ethyl, trifluoromethyl, and fluoro; and phenyl, benzyl, naphthyl, and phenethyl, wherein the phenyl, benzyl, naphthyl, and phenethyl are optionally substituted on their aromatic ring system with 1-3 substituents Y as defined above, with the proviso that R₆ is not a 2-methylphenyl;

R₇ is chosen from: hydrogen; C$_{1-6}$ linear alkyl optionally substituted with 1-3 fluorine atoms; and isopropyl;

R₈ is chosen from: C$_{2-6}$ alkyl substituted with at least one substituent chosen from hydroxy, amino, and 1-3 fluorine atoms; C$_{7-10}$ branched alkyl; C$_{3-8}$ cycloalkyl, C$_{5-8}$ heterocycloalkyl having at least one heteroatom chosen from nitrogen, oxygen, and sulfur, C$_{3-8}$-cycloalkyl-C$_{1-2}$-alkyl, C$_{5-7}$-heterocycloalkyl-C$_{1-2}$-alkyl having at least one heteroatom chosen from nitrogen, oxygen, and sulfur, C$_{5-10}$-bicycloalkyl, C$_{5-10}$-bicycloalkyl-C$_{1-2}$-alkyl, C$_{5-10}$-heterobicycloalkyl-C$_{1-2}$-alkyl having at least one heteroatom chosen from nitrogen, oxygen, and sulfur, C$_{6-10}$-tricycloalkyl, C$_{6-10}$-tricycloalkyl-C$_{1-2}$-alkyl, C$_{6-10}$-heterotricycloalkyl-C$_{1-2}$-alkyl having at least one heteroatom chosen from nitrogen, oxygen, and sulfur, which groups are optionally substituted with 1-5 substituents chosen from methyl, hydroxy, ethyl, amino, hydroxymethyl, trifluoromethyl, and fluoro; phenyl substituted with 1-5 substituents Y as defined above; naphthyl, 1,2,3,4-tetrahydronaphthyl, and indanyl, which naphthyl, 1,2,3,4-tetrahydronaphthyl, and indanyl groups are optionally substituted with 1-3 substituents Y as defined above; phenyl-C$_{1-3}$-alkyl and diphenyl-C$_{1-3}$-alkyl, which groups are optionally substituted on their phenyl ring with 1-5 substituents Y as defined above; benzyl substituted with 1-5 substituents Y as defined above; heteroaryl having at least one heteroatom chosen from nitrogen, oxygen, and sulfur, heteroarylmethyl having at least one heteroatom chosen from nitrogen, oxygen, and sulfur, naphthylmethyl, heteroarylethyl having at least one heteroatom chosen from nitrogen, oxygen, and sulfur, which heteroaryl, heteroarylmethyl, naphthylmethyl, and heteroarylethyl groups are optionally substituted with 1-3 substituents Y as defined above; piperidinyl; azepanyl; morpholinyl; azabicyclo[3.3.0]octanyl; 4-hydroxypiperidinyl; and pyrrolidinyl, with the proviso that R₈ is neither 6-methoxy-benzothiazol-2-yl nor [3-chloro-5-(trifluoromethyl)pyrid-2-yl]methyl;

or R₇ and R₈, together with the nitrogen atom to which they are bonded, form a saturated or unsaturated, nonaromatic or partly aromatic monocyclic, bicyclic or tricyclic heterocyclic group having at least one heteroatom chosen from nitrogen, oxygen, and sulfur having 7 to 10 ring atoms, which saturated or unsaturated, nonaromatic or partly aromatic monocyclic, bicyclic or tricyclic heterocyclic group is optionally substituted with 1-5 substituents chosen from C$_{1-3}$ alkyl, hydroxy, methoxy, cyano, phenyl, trifluoromethyl, and halogen;

or R₇ and R₈, together with the nitrogen atom to which they are bonded, form a saturated monocyclic heterocyclic group, having 5 to 6 ring atoms and having at least one heteroatom chosen from nitrogen, oxygen, and sulfur, which heterocyclic group is substituted with 1-5 substituents chosen from C$_{1-3}$ alkyl, hydroxy, amino, phenyl, benzyl, and fluoro, with the proviso that R₇ and R₈, together with the nitrogen atom to which they are bonded, do not form a trimethyl-substituted azabicyclo[3.2.1]octanylgroup, The invention also relates to racemates, mixtures of diastereomers as well as the individual stereoisomers of the compounds having formula (I).

In the description of the substituents the abbreviation 'alkyl' means a linear or branched alkyl group. For example, C$_{1-3}$-alkyl means methyl, ethyl, n-propyl or isopropyl. The abbreviation 'heteroaryl' means monocyclic or fused bicyclic heteroaromatic (i.e., (N, O, S) heteroatom containing rings) groups, including but not limited to furyl, thienyl, pyrrolyl, oxazolyl, thiazolyl, imidazolyl, pyrazolyl, isoxazolyl, isothiazolyl, pyridyl, pyridazinyl, pyrimidinyl, pyrazinyl, 1,3,5-triazinyl, indazolyl, indolyl, indolizinyl, isoindolyl, benzo[b]furanyl, benzo[b]thiophenyl, 1,3-benzodioxolyl, 2,3-dihydro-1,4-benzodioxinyl, benzimidazolyl, benzthiazolyl, purinyl, quinolinyl, isochinolyl, 1,2,3,4-tetrahydroquinolinyl, 1,2,3,4-tetrahydroisoquinolinyl, chinolyl, phtalazinyl, quinazolinyl, quinoxalinyl, 1,8-naphthyridinyl, with the exclusion of the quinolin-2-one group. The abbreviation 'halogen' means chloro, fluoro, bromo or iodo. The abbreviation 'C$_{3-8}$-cycloalkyl' means cyclopropyl, cyclobutyl, cyclopentyl, cyclohexyl, cycloheptyl or cyclooctyl. The abbreviation 'C$_{5-8}$ heterocycloalkyl' refers to (N, O, S) heteroatom containing rings, including but not limited to piperidinyl, morpholinyl, azepanyl, pyrrolidinyl, thiomorpholinyl, piperazinyl, tetrahydrofuryl, tetrahydropyranyl. The abbreviation 'C$_{5-10}$ bicycloalkyl group' refers to carbo-bicyclic ring systems, including but not limited to bicyclo[2.2.1]heptanyl, bicyclo[3.3.0]octanyl or the bicyclo[3.1.1]heptanyl group. The abbreviation 'C$_{6-10}$ tricycloalkyl group' refers to carbotricyclic ring systems such as the 1-adamantyl, noradamantyl or the 2-adamantyl group. The abbreviation 'C$_{2-4}$ heteroalkyl' refers to (N, O, S) heteroatom containing linear or branched C$_{2-4}$-alkyl groups, including but not limited to methoxymethyl, dimethylaminomethyl and ethylsulfanylmethyl.

Prodrugs of the compounds mentioned above are in the scope of the present invention. Prodrugs are therapeutic agents which are inactive per se but are transformed into one or more active metabolites. Prodrugs are bioreversible derivatives of drug molecules used to overcome some barriers to the utility of the parent drug molecule. These barriers include, but are not limited to, solubility, permeability, stability, presystemic metabolism and targeting limitations (Medicinal Chemistry: Principles and Practice, 1994, ISBN 0-85186-494-5, Ed.: F. D. King, p. 215; J. Stella, "*Prodrugs as therapeutics*", Expert Opin. Ther. Patents, 14(3), 277-280, 2004; P. Ettmayer et al., "*Lessons learned from marketed and investigational prodrugs*", J. Med. Chem., 47, 2393-2404, 2004). Pro-drugs, i.e. compounds which when administered to humans by any known route, are metabolised to compounds having formula (I), belong to the invention. For example, this relates to compounds with primary or secondary amino or hydroxy groups. Such compounds can be reacted with organic acids to yield compounds having formula (I) wherein an additional group is present which is easily removed after administration, for instance, but not limited to amidine, enamine, a Mannich base, a hydroxyl-methylene derivative, an O-(acyloxymethylene carbamate) derivative, carbamate, ester, amide or enaminone.

N-oxides of the compounds mentioned above are in the scope of the present invention. Tertiary amines may or may not give rise to N-oxide metabolites. The extend to what N-oxidation takes place varies from trace amounts to a near quantitative conversion. N-oxides may be more active than their corresponding tertiary amines or less active. Whilst N-oxides are easily reduced to their corresponding tertiary amines by chemical means, in the human body this happens to varying degrees. Some N-oxides undergo nearly quantitative reductive conversion to the corresponding tertiary amines, in other cases the conversion is a mere trace reaction or even completely absent. (M. H. Bickel: "*The pharmacology and Biochemistry of N-oxides*", Pharmacological Reviews, 21(4), 325-355, 1969).

In another embodiment, the invention relates to compounds of formula (1):

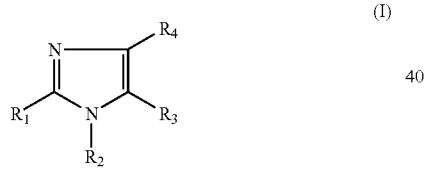

(I)

wherein:
R$_1$ is chosen from: halogen; C$_{1-3}$-alkyl optionally substituted with at least one group chosen from 1-3 fluorine atoms, hydroxy, and amino; C$_{2-3}$-alkynyl and C$_{2-3}$-alkenyl, which C$_{2-3}$-alkynyl and, C$_{2-3}$-alkenyl are optionally substituted with 1-3 fluorine atoms; acetyl; cyclopropyl; cyano; methylsulfonyl; ethylsulfonyl; methylsulfinyl; ethylsulfinyl; trifluoromethylsulfanyl; methylsulfanyl; ethylsulfanyl; formyl; and C$_{2-4}$-heteroalkyl; and R$_2$, R$_3$, and R$_4$ are as defined in claim 1.

In another embodiment, the invention relates to compounds of formula (I):

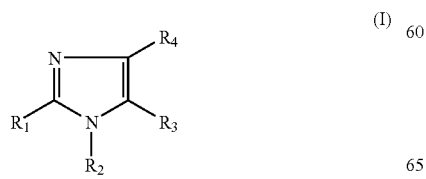

(I)

wherein:
R$_3$ is chosen from: hydrogen; halogen; formyl; methylsulfonyl; ethylsulfonyl; methylsulfinyl; ethylsulfinyl; trifluoromethylsulfanyl; methylsulfanyl; ethylsulfanyl; cyano; C$_{1-6}$alkyl optionally substituted with at least one substituent chosen from 1-3 fluorine atoms, hydroxy, and amino; C$_{2-6}$-alkynyl, C$_{2-6}$-alkenyl, C$_{1-6}$alkanoyl, C$_{3-8}$-cycloalkyl, C$_{5-8}$-heterocycloalkyl having at least one heteroatom chosen from nitrogen, oxygen, and sulfur, C$_{2-6}$-heteroalkyl having at least one heteroatom chosen from nitrogen, oxygen, and sulfur, wherein the C$_{2-6}$-alkynyl, C$_{2-6}$-alkenyl, C$_{1-6}$-alkanoyl, C$_{3-8}$-cycloalkyl, C$_{5-8}$-heterocycloalkyl, and C$_{2-6}$-heteroalkyl are optionally substituted with at least one substituent chosen from 1-3 methyl groups, ethyl, amino, hydroxy, and 1-3 fluorine atoms; phenyl optionally substituted with 1-5 substituents Y, as defined above; heteroaryls having at least one heteroatom chosen from nitrogen, oxygen, and sulfur optionally substituted with 1, 2 or 3 substituents Y, as defined above; benzyl and heteroarylmethyl wherein the benzyl and heteroarylmethyl are optionally substituted with 1, 2 or 3 substituents Y, as defined above;
R$_4$ has the formula (ii)

(ii)

wherein
R$_7$ is chosen from: hydrogen; C$_{1-6}$ linear alkyl; and isopropyl;
R$_8$ is chosen from: C$_{2-6}$ alkyl substituted with at least one substituent chosen from hydroxy, amino, and 1-3 fluorine atoms; C$_{7-10}$ branched alkyl; C$_{3-8}$ cycloalkyl; C$_{5-8}$ heterocycloalkyl having at least one heteroatom chosen from nitrogen, oxygen, and sulfur, C$_{3-8}$-cycloalkyl-C$_{1-2}$-alkyl, C$_{5-7}$-heterocycloalkyl-C$_{1-2}$-alkyl having at least one heteroatom chosen from nitrogen, oxygen, and sulfur, C$_{5-10}$ bicycloalkyl, C$_{5-10}$-bicycloalkyl-C$_{1-2}$-alkyl, C$_{5-10}$-heterobicycloalkyl-C$_{1-2}$-alkyl, C$_{6-10}$ tricycloalkyl, C$_{6-10}$-tricycloalkyl-C$_{1-2}$-alkyl, C$_{6-10}$-heterotricycloalkyl-C$_{1-2}$-alkyl having at least one heteroatom chosen from nitrogen, oxygen, and sulfur, which groups are optionally substituted with 1-5 substituents chosen from methyl, hydroxy, ethyl, amino, hydroxymethyl, trifluoromethyl, and fluoro; phenyl substituted with 1-5 substituents Y as defined above; naphthyl, 1,2,3,4-tetrahydronaphthyl, and indanyl, which groups are optionally substituted with 1-3 substituents Y, as defined above; phenyl-C$_{1-3}$-alkyl and diphenyl-C$_{1-3}$-alkyl, which groups are optionally substituted on their phenyl ring with 1-5 substituents Y, as defined above; benzyl substituted with 1-5 substituents Y, as defined above; heteroaryl having at least one heteroatom chosen from nitrogen, oxygen, and sulfur, heteroarylmethyl having at least one heteroatom chosen from nitrogen, oxygen, and sulfur, heteroarylethyl having at least one heteroatom chosen from nitrogen, oxygen, and sulfur, which heteroaryl, heteroarylmethyl, and heteroarylethyl group are optionally substituted with 1-3 substituents Y, as defined above;

piperidinyl; azepanyl; morpholinyl; azabicyclo [3.3.0]octanyl; 4-hydroxypiperidinyl; and pyrrolidinyl, with the proviso that $R_8$ is neither 6-methoxy-benzothiazol-2-yl nor [3-chloro-5-(trifluoromethyl)pyrid-2-yl]methyl;

or $R_7$ and $R_8$, together with the nitrogen atom to which they are bonded, form a saturated or unsaturated, nonaromatic or partly aromatic, monocyclic, bicyclic or tricyclic heterocyclic group having at least one heteroatom chosen from nitrogen, oxygen, and sulfur having 7 to 10 ring atoms, which heterocyclic group is optionally substituted with at least one substituent chosen from one or two $C_{1-3}$ alkyl groups, hydroxy, phenyl, trimethylfluoromethyl, benzyl, diphenylmethyl, and halogen or $R_7$ and $R_8$, together with the nitrogen atom to which they are bonded, form a saturated monocyclic heterocyclic group, having 5 to 6 ring atoms and having at least one heteroatom chosen from nitrogen, oxygen, and sulfur, which heterocyclic group is substituted with at least one substituent chosen from 1-3 $C_{1-3}$ alkyl groups, hydroxy, and 1-2 fluoro atoms, with the proviso that $R_7$ and $R_8$, together with the nitrogen atom to which they are bonded, do not form a trimethyl-substituted azabicyclo [3.2.1]octanyl.

In another embodiment, the invention relates to compounds of formula (I)

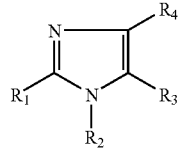

(I)

wherein:
$R_1$ is chosen from: halogen and $C_{1-3}$-alkyl optionally substituted with at least substituent chosen from 1-3 fluorine atoms and hydroxy; $C_{2-3}$-alkynyl; $C_{2-3}$-alkenyl; acetyl; cyclopropyl; cyano, methylsulfonyl; methylsulfinyl; methylsulfanyl; and $C_{2-4}$-heteroalkyl having at least one heteroatom chosen from nitrogen, oxygen, and sulfur;

$R_2$ is chosen from:
phenyl optionally substituted with 1, 2, 3, 4 or 5 substituents Y as defined above; monocyclic heteroaryl having at least one heteroatom chosen from nitrogen, oxygen, and sulfur and being optionally substituted with 1, 2 or 3 substituents Y, as defined above, with the proviso that $R_2$ is not 6-methyl-2-pyridyl;
mono-unsaturated and fully saturated 4-10 membered monocyclic, fused bicyclic or fused tricyclic carbocyclic ring systems and mono-unsaturated and fully saturated 4-10 membered monocyclic, fused bicyclic and fused tricyclic heterocyclic having at least one heteroatom chosen from nitrogen, oxygen, and sulfur ring systems, which carbocyclic and heterocyclic ring systems are optionally substituted with 1-5 substituents chosen from methyl, ethyl, amino, hydroxy, and fluoro;
a group of formula $CH_2—R_5$ wherein $R_5$ is chosen from phenyl substituted with 1, 2, 3, 4 or 5 substituents Y as defined above; heteroaryl having at least one heteroatom chosen from nitrogen, oxygen, and sulfur, 1,2,3,4-tetrahydronaphthyl, and indanyl, which heteroaryl, 1,2,3,4-tetrahydronaphthyl, and indanyl are optionally substituted with 1, 2 or 3 substituents Y as defined above; mono-unsaturated and fully saturated monocyclic, fused bicyclic and fused tricyclic 4-10 membered carbocyclic ring systems, mono-unsaturated and fully saturated 4-10 membered monocyclic, fused bicyclic and fused tricyclic heterocyclic ring systems, which carbocyclic and heterocyclic rings systems having at least one heteroatom chosen from nitrogen, oxygen, and sulfur are optionally substituted with 1-3 methyl groups, ethyl, amino, hydroxy, and fluoro, $R_3$ is chosen from hydrogen; halogen; methylsulfanyl; cyano; $C_{1-6}$-alkyl optionally substituted with at least one substituent chosen from 1-3 fluorine atoms, hydroxy, and amino; $C_{2-6}$-alkynyl and $C_{2-6}$-alkenyl, which groups are optionally substituted with 1-3 fluorine atoms;

$R_4$ has the formula (ii)

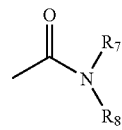

(ii)

wherein
$R_7$ is chosen from hydrogen and $C_{1-3}$ linear alkyl;
$R_8$ is chosen from $C_{2-6}$ alkyl substituted with at least one substituent chosen from hydroxy, amino, and 1-3 fluorine atoms; $C_{7-10}$ branched alkyl, $C_{3-8}$ cycloalkyl, $C_{5-8}$ heterocycloalkyl having at least one heteroatom chosen from nitrogen, oxygen, and sulfur, $C_{3-8}$-cycloalkyl-$C_{1-2}$-alkyl, $C_{5-7}$-heterocycloalkyl-$C_{1-2}$-alkyl having at least one heteroatom chosen from nitrogen, oxygen, and sulfur, $C_{5-10}$ bicycloalkyl, $C_{5-10}$-bicycloalkyl-$C_{1-2}$-alkyl, $C_{5-10}$-heterobicycloalkyl-$C_{1-2}$-alkyl having at least one heteroatom chosen from nitrogen, oxygen, and sulfur, $C_{6-10}$ tricycloalkyl, $C_{6-10}$-tricycloalkyl-$C_{1-2}$-alkyl, and $C_{6-10}$-heterotricycloalkyl-$C_{1-2}$-alkyl having at least one heteroatom chosen from nitrogen, oxygen, and sulfur, which groups are optionally substituted with 1-5 substituents chosen from methyl, hydroxy, ethyl, amino, hydroxymethyl, trifluoromethyl, and fluoro; phenyl substituted with 1-5 substituents Y as defined above; naphthyl, 1,2,3,4-tetrahydronaphthyl, and indanyl, which groups are optionally substituted with 1-3 substituents Y, as defined above; phenyl-$C_{1-3}$-alkyl, and diphenyl-$C_{1-3}$-alkyl, which groups are optionally substituted on their phenyl ring with 1-5 substituents Y, as defined above; benzyl substituted with 1-5 substituents Y; heteroaryl having at least one heteroatom chosen from nitrogen, oxygen, and sulfur, heteroaryl methyl having at least one heteroatom chosen from nitrogen, oxygen, and sulfur, and heteroarylethyl having at least one heteroatom chosen from nitrogen, oxygen, and sulfur, which heteroaryl, heteroarylmethyl, and heteroarylethyl are optionally substituted with 1-3 substituents Y, as defined above; piperidinyl; azepanyl; morpholinyl; azabicyclo[3.3.0]octanyl; 4-hydroxypiperidinyl; and pyrrolidinyl,
with the proviso that $R_8$ is neither 6-methoxy-benzothiazol-2-yl nor [3-chloro-5-(trifluoromethyl)pyrid-2-yl]methyl.

In another embodiment, the invention relates to compounds of formula (I)

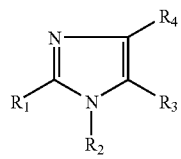

(I)

wherein:
$R_1$ is chosen from: halogen; $C_{1-3}$-alkyl optionally substituted with at least one substituent chosen from 1-3 fluoro atoms and hydroxy; cyano; and methylsulfanyl;
$R_2$ is chosen from: mono-unsaturated and fully saturated 5-7 membered monocyclic carbocyclic ring systems substituted with 1-5 substituents chosen from methyl, ethyl, amino, hydroxyl, and fluoro; phenyl optionally substituted with 1, 2, 3, 4 or 5 substituents Y, as defined above;
$R_3$ is chosen from: hydrogen; halogen; methylsulfanyl; cyano; $C_{1-6}$-alkyl optionally substituted with at least one substituent chosen from 1-3 fluorine atoms, hydroxyl, and amino;
$R_4$ has the formula (ii)

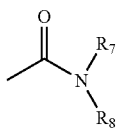

(ii)

wherein
$R_7$ is chosen from hydrogen and methyl;
$R_8$ is chosen from $C_{2-6}$ alkyl substituted with 1-3 fluoro atoms; $C_{7-10}$ branched alkyl, $C_{3-8}$ cycloalkyl, $C_{5-8}$ heterocycloalkyl having at least one heteroatom chosen from nitrogen, oxygen, and sulfur, $C_{3-8}$-cycloalkyl-$C_{1-2}$alkyl, $C_{5-7}$-heterocycloalkyl-$C_{1-2}$-alkyl having at least one heteroatom chosen from nitrogen, oxygen, and sulfur, $C_{5-10}$-bicycloalkyl, $C_{5-10}$-bicycloalkyl-$C_{1-2}$-alkyl, $C_{5-10}$-heterobicycloalkyl-$C_{1-2}$-alkyl having at least one heteroatom chosen from nitrogen, oxygen, and sulfur, $C_{6-10}$ tricycloalkyl, $C_{6-10}$-tricycloalkyl-$C_{1-2}$-alkyl, and $C_{6-10}$-heterotricycloalkyl-$C_{1-2}$-alkyl having at least one heteroatom chosen from nitrogen, oxygen, and sulfur, which groups are optionally substituted with 1-5 substituents chosen from methyl, hydroxy, ethyl, amino, hydroxymethyl, trifluoromethyl, and fluoro; phenyl group substituted with 1-5 substituents Y as defined above; naphthyl, 1,2,3,4-tetrahydronaphthyl, and indanyl, which groups are optionally substituted with 1-3 substituents Y, as defined above; phenyl-$C_{1-3}$-alkyl and diphenyl-$C_{1-3}$-alkyl, which groups are optionally substituted on their phenyl ring with 1-5 substituents Y as defined above; benzyl substituted with 1-5 substituents Y as defined above; and heteroaryl, heteroarylmethyl, and heteroarylethyl having at least one heteroatom chosen from nitrogen, oxygen, and sulfur, which groups are optionally substituted with 1-3 substituents Y, as defined above,
with the proviso that $R_8$ is neither 6-methoxy-benzothiazol-2-yl nor [3-chloro-5-(trifluoromethyl)pyrid-2-yl]methyl.

In another embodiment, the invention relates to compounds of formula (I)

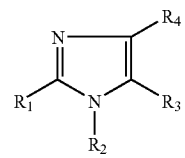

(I)

wherein:
$R_1$ is chosen: from halogen and $C_{1-2}$-alkyl optionally substituted with 1-3 fluoro atoms; cyano; and methylsulfanyl;
$R_2$ is chosen from: saturated six-membered monocyclic carbocyclic rings; and phenyl optionally substituted with 1, 2 or 3 substituents Y, as defined above;
$R_3$ is chosen from: hydrogen; halogen; methylsulfanyl; cyano; and $C_{1-4}$-alkyl optionally substituted with 1-3 fluoro atoms,
$R_4$ has the formula (ii)

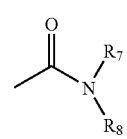

(ii)

wherein
$R_7$ is chosen from: hydrogen and methyl;
$R_8$ is chosen from: $C_{2-6}$ alkyl substituted with 1-3 fluoro atoms; $C_{7-10}$ branched alkyl, $C_{3-8}$ cycloalkyl, $C_{5-8}$ heterocycloalkyl having at least one heteroatom chosen from nitrogen, oxygen, and sulfur, $C_{3-8}$-cycloalkyl-$C_{1-2}$-alkyl, $C_{5-7}$-heterocycloalkyl-$C_{1-2}$-alkyl having at least one heteroatom chosen from nitrogen, oxygen, and sulfur, $C_{5-10}$ bicycloalkyl, $C_{5-10}$-bicycloalkyl-$C_{1-2}$-alkyl, $C_{5-10}$-heterobicycloalkyl-$C_{1-2}$-alkyl having at least one heteroatom chosen from nitrogen, oxygen, and sulfur, $C_{6-10}$ tricycloalkyl, $C_{6-10}$-tricycloalkyl-$C_{1-2}$-alkyl, and $C_{6-10}$-heterotricycloalkyl-$C_{1-2}$-alkyl having at least one heteroatom chosen from nitrogen, oxygen, and sulfur, which groups are optionally substituted with 1-5 substituents chosen from methyl, hydroxy, ethyl, amino, hydroxymethyl, trifluoromethyl, and fluoro; phenyl substituted with 1-3 substituents Y as defined above; naphthyl optionally substituted with 1-3 substituents Y as defined above; phenyl-$C_{1-2}$-alkyl optionally substituted on the phenyl ring with 1-3 substituents Y as defined above; and benzyl substituted with 1-5 substituents Y as defined above.

Another embodiment provides compounds of formula (XIV)

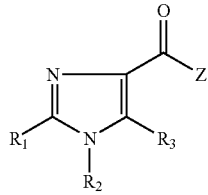

(XIV)

or a tautomer, a stereoisomer, or N-oxides thereof, or a pharmacologically acceptable salt, hydrate or solvate of any of the foregoing
wherein:
$R_1$ is chosen from: halogen and $C_{1-3}$-alkyl optionally substituted with at least one substituent chosen from 1-3- fluorine atoms, hydroxy, and amino; $C_{2-3}$-alkynyl and $C_{2-3}$-alkenyl, which $C_{2-3}$-alkynyl and $C_{2-3}$-alkenyl are optionally substituted with 1-3 fluorine atoms; acetyl; cyclopropyl; cyano; methylsulfonyl; ethylsulfonyl; methylsulfinyl; ethylsulfinyl trifluoromethylsulfanyl; methylsulfanyl; ethylsulfanyl; formyl; and $C_{2-4}$-heteroalkyl having at least one heteroatom chosen from nitrogen, oxygen, and sulfur;

$R_2$ is chosen from:
phenyl optionally substituted with 1, 2, 3, 4 or 5 substituents Y, which can be the same or different, Y being chosen from methyl, ethyl, propyl, methoxy, ethoxy, hydroxy, chloro, iodo, bromo, fluoro, trifluoromethyl, trifluoromethoxy, methylsulfonyl, carbamoyl, phenyl, and cyano; heteroaryl having at least one heteroatom chosen from nitrogen, oxygen, and sulfur optionally substituted with 1, 2 or 3 substituents Y as defined above, with the proviso that $R_2$ is not 6-methyl-2-pyridyl;

mono-unsaturated and fully saturated 4-10 membered monocyclic, fused bicyclic and fused tricyclic carbocyclic ring systems and mono-unsaturated and fully saturated 4-10 membered monocyclic, fused bicyclic and fused tricyclic heterocyclic ring systems, which carbocyclic and heterocyclic ring systems having at least one heteroatom chosen from nitrogen, oxygen, and sulfur are optionally substituted with 1-5 substituents chosen from methyl, ethyl, amino, hydroxyl, and fluoro;

a group of formula $CH_2$—$R_5$ wherein $R_5$ is chosen from: phenyl substituted with 1, 2, 3, 4 or 5 substituents Y as defined above, heteroaryl having at least one heteroatom chosen from nitrogen, oxygen, and sulfur, 1,2,3,4-tetrahydronaphthyl, and indanyl, which heteroaryl, 1,2,3,4-tetrahydronaphthyl and indanyl are optionally substituted with 1, 2 or 3 substituents Y as defined above;

mono-unsaturated and fully saturated monocyclic, fused bicyclic and fused tricyclic 4-10 membered carbocyclic ring systems;

mono-unsaturated and fully saturated 4-10 membered monocyclic, fused bicyclic and fused tricyclic heterocyclic ring systems having at least one heteroatom chosen from nitrogen, oxygen, and sulfur, which carbocyclic and heterocyclic ring systems are optionally substituted with 1-5 substituents chosen from methyl, ethyl, amino, hydroxy, and fluoro; and methylsulfonylaminoalkyl; methylsulfonylalkyl; and acetamidoalkyl, with the proviso that $R_2$ is not phenyl, 4-methylphenyl, or 4-methoxyphenyl;

$R_3$ is chosen from: hydrogen; halogen; formyl; $C_{1-6}$-alkylsulfonyl; $C_{1-6}$-alkylsulfinyl; $C_{1-6}$-alkylsulfanyl; trifluoromethylsulfanyl; benzylsulfanyl; cyano; $C_{1-8}$-alkyl optionally substituted with 1-5 substituents chosen from fluoro, hydroxyl, and amino; $C_{2-6}$-alkynyl, $C_{2-6}$-alkenyl, $C_{1-6}$-alkanoyl, $C_{3-8}$-cycloalkyl, $C_{5-8}$-heterocycloalkyl having at least one heteroatom chosen from nitrogen, oxygen, and sulfur, and $C_{2-6}$-heteroalkyl having at least one heteroatom chosen from nitrogen, oxygen, and sulfur, which groups are optionally substituted with at least one substituent chosen from 1-3 methyl groups, ethyl, amino, hydroxy, and 1-3 fluorine atoms; phenyl substituted with 1-5 substituents Y as defined above; heteroaryl having at least one heteroatom chosen from nitrogen, oxygen, and sulfur optionally substituted with 1, 2 or 3 substituents Y as defined above; benzyl and heteroarylmethyl having at least one heteroatom chosen from nitrogen, oxygen, and sulfur, which benzyl and heteroarylmethyl are optionally substituted with 1, 2 or 3 substituents Y as defined above;

Z is chosen from chloro; $C_{1-3}$ alkyl; hydroxy; —O—Na; —O—K; —O—Li; —O—Cs; and N-methoxy-N-methyl-amino.

Finally, the invention also relates to compounds having formula (I) wherein $R_2$ represents a saturated six-membered monocyclic carbocyclic ring or $R_2$ represents a phenyl group which may be substituted with 1, 2, 3, 4 or 5 substituents Y, which can be the same or different, chosen from methyl, ethyl, propyl, methoxy, ethoxy, hydroxy, chloro, iodo, bromo, fluoro, trifluoromethyl, trifluoromethoxy, methylsulfonyl, carbamoyl, phenyl and cyano, and all other symbols have the meanings as described above.

General Aspects of Syntheses

Compounds of formula (I) may be prepared by different methodologies. The selection of the particular method depends on factors such as the compatibility of functional groups with the reagents used, the possibility to use protecting groups, catalysts, activating and coupling reagents and the ultimate structural features present in the final compound being prepared.

Imidazole derivatives can be obtained according to methods known. Relevant articles are:

a) Gomez-Sanchez et al., *J. Heterocyclic Chem.* (1987), 24, 1757-1763.

b) Matsuura et al., *J. Chem. Soc. Perkin Trans. I* (1991), 11, 2821-2826 c) Ueda et al., *Tetrahedron Lett.* (1988), 29, 4607-4610 d) Gupta et al., *Eur. J. Med. Chem.* (2004), 39, 805-814 e) Van Berkel et al. *Tetrahedron Lett.* (2004), 45, 7659-7662 f) Haberhauer and Rominger, *Tetrahedron Lett.* (2002), 43, 6335-6338 g) Dell'Erba et al., *Tetrahedron* (1997), 53, 2125-2136 h) Lipshutz et al., *Tetrahedron Lett.* (1992), 33, 5865-5868

Compounds of general formula (I) can be obtained according to the procedures outlined in Schemes 1-6.

Scheme 1:

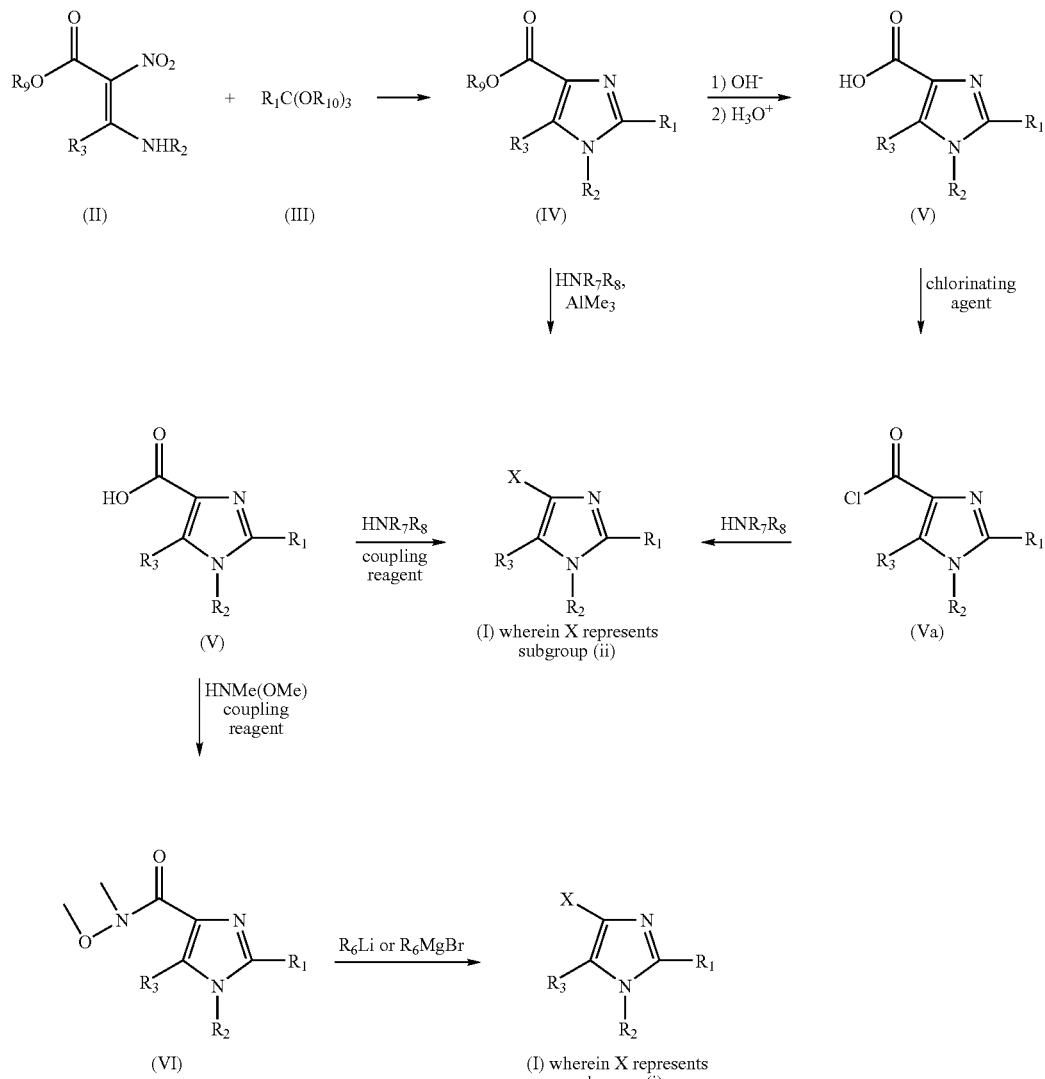

The symbols $R_1$–$R_8$ have the meanings as given above on pages 2–5, $R_9$ and $R_{10}$ represent alkyl($C_{1-3}$)

Nitroenamine derivatives of general formula (II) can be prepared according to the procedure published by Gomez-Sanchez et al., *J. Heterocyclic Chem.* (1987), 24, 1757-1763. Nitroenamine derivatives of general formula (II) can be reacted with ortho-esters of general formula (III) to give imidazole derivatives of general formula (IV) (Scheme 1). Subsequent basic ester hydrolysis, for example using lithium hydroxide (LiOH), NaOH, KOH or CsOH can provide intermediate imidazolecarboxylic acid alkali salts, which can be acidified by an acid such as aqueous hydrochloride (HCl) to give imidazolecarboxylic acid derivatives of general formula (V). Compounds of general formula (IV) can be amidated with an amine of general formula $R_7R_8NH$ into a compound of general formula (I) wherein X represents subgroup (ii) as defined above. Such amidations can be catalyzed by trimethylaluminum $(CH_3)_3Al$. (For more information on aluminum-mediated conversion of esters to amides, see: J. I. Levin, E. Turos, S. M. Weinreb, *Synth. Commun.* (1982), 12, 989-993.). Imidazolecarboxylic acid derivatives of general formula (V) or their corresponding alkali salts can be reacted with an amine of general formula $R_7R_8NH$ into a compound of general formula (I) wherein X represents subgroup (ii) as defined above. This particular reaction can proceed via activating and coupling methods such as formation of an active ester, or in the presence of a so-called coupling reagent, such as for example, DCC, HBTU (O-benzotriazol-1-yl-N,N,N',N'-tetramethyluronium hexafluorophosphate), TBTU, HOAt (N-hydroxy-7-azabenzotriazole), BOP, CIP (2-chloro-1,3-dimethylimi-dazolinium hexafluorophosphate), 2-chloro-1,3-dimethylimidazolinium chloride, PyAOP (7-azabenzotriazol-1-yloxytris(pyrrolidino)-phosphonium hexafluorophosphate) and the like. (For more information on activating and coupling methods see a) M. Bodanszky, A. Bodanszky: The Practice of Peptide Synthesis, Springer-Verlag, New York, 1994; ISBN: 0-387-57505-7; b) K. Akaji et al., *Tetrahedron Lett.* (1994), 35, 3315-3318; c) F. Albericio et al., *Tetrahedron Lett.* (1997), 38, 4853-4856; d) C. Montalbetti and V. Falque, *Tetrahedron* (2005), 61, 10827-10852).

Alternatively, a compound having general formula (V) or the corresponding alkali salts can be reacted with a so-called halogenating agent such as for example thionyl chloride (SOCl$_2$) or oxalyl chloride. This reaction gives the corresponding carbonyl chloride (acid chloride) (Va) which can subsequently be reacted with a compound having formula R$_7$R$_8$NH wherein R$_7$ and R$_8$ have the meanings as described above, to give a compound of general formula (I) wherein X represents subgroup (ii) as defined above. Such reactions can be catalyzed by pyridine or 4-dimethylaminopyridine (DMAP).

A compound having general formula (V) can be reacted with N-methoxy-N-methylamine in the presence of a coupling reagent to yield the corresponding N-methoxy-N-methylamide of general formula (VI) and subsequently reacted with a lithium reagent of general formula R$_6$—Li or a Grignard reagent to give a compound of general formula (I), wherein X represents subgroup (i) as defined above.

Scheme 2:

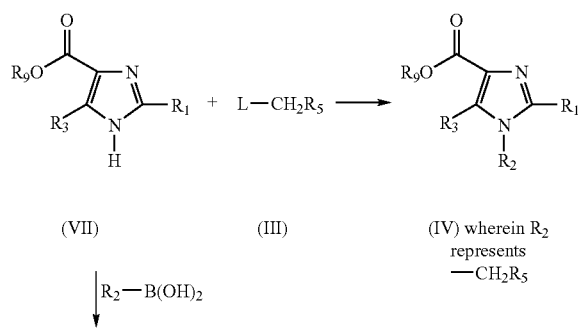

(VII)  (III)  (IV) wherein R$_2$ represents —CH$_2$R$_5$

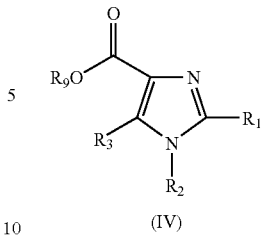

(IV)

The symbols R$_1$–R$_5$ have the meanings as given above as given above on pages 2–5, R$_9$ represents alkyl(C$_{1-3}$). In the compounds of general formula R$_2$—B(OH)$_2$, R$_2$ represents an optionally substituted phenyl or heteroaryl group, a so-called Suzuki reagent.

Alternatively, a compound having general formula (VII) can be reacted with a compound of general formula (VIII), wherein L represents a so-called leaving group, such as chloro, bromo, iodo or mesyloxy (Scheme 2). A compound having general formula (VII) can also be reacted with a methylsulfonylaminoalkyl halogenide or methylsulfonylalkyl halogenide to add a methylsulfonylaminoalkyl group or methylsulfonylalkyl group to the 1-position of the imidazole nucleus. Such reactions can be carried out in the presence of a base, such as sodium hydride or potassium carbonate to facilitate the nucleophilic attack of compound (VII) to produce a compound of formula (IV), wherein R$_2$ represents a group —CH$_2$R$_5$ and R$_5$ has the abovementioned meaning.

Alternatively, a compound having general formula (VII) can be reacted with compound of general formula R$_2$—B(OH)$_2$ wherein R$_2$ represents an optionally substituted phenyl or heteroaryl group, a so-called Suzuki reagent, to produce a compound of general formula (IV). Compounds of general formula (IV) can be converted to compounds of general formula (I) according to Scheme 1. Such reactions may be metal-catalyzed.

Scheme 3:

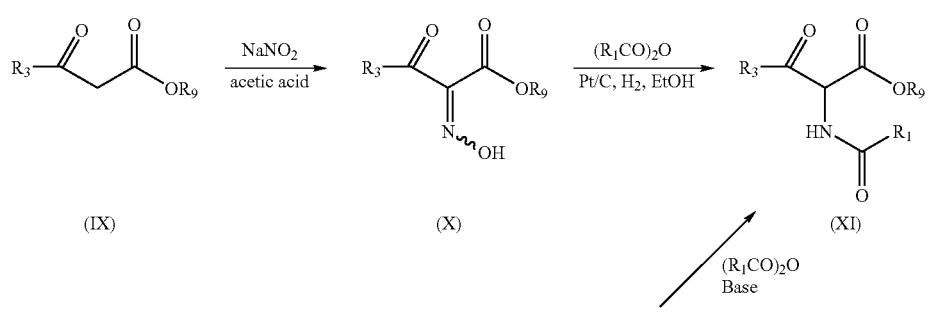

(IX)  (X)  (XI)

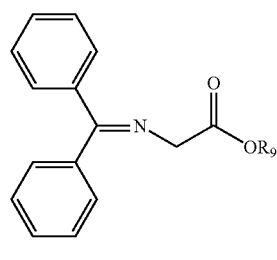

(XII)  (XIII)

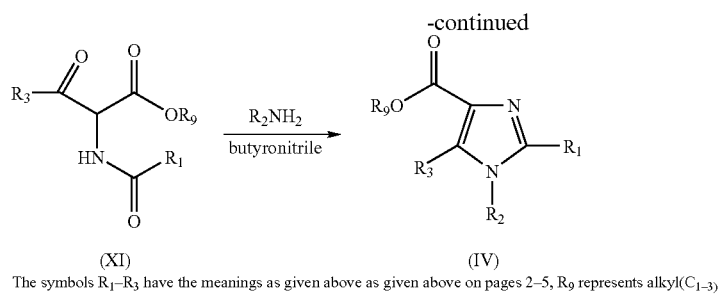

The symbols $R_1$–$R_3$ have the meanings as given above as given above on pages 2–5, $R_9$ represents alkyl($C_{1-3}$)

A compound having general formula (IX) can be reacted with a nitrite derivative such as sodium nitrite (NaNO$_2$) to give a compound of general formula (X). (Scheme 3). A compound having general formula (X) can be reacted with an anhydride of general formula (R$_1$CO)$_2$O in the presence of a reducing agent such as hydrogen and a catalyst such as Pd on carbon (Pd/C) and the like, in an inert organic solvent such as ethanol to give a compound of general formula (XI). A compound having general formula (XI) can be reacted with an amine of general formula R$_2$NH$_2$ in an inert solvent such as butyronitrile, to give a compound of general formula (IV). Compounds of general formula (IV) can be converted to compounds of general formula (I) according to Scheme 1.

Alternatively, a compound of general formula (XI) can be obtained in a two-pot reaction from a compound of general formula (XII). A compound of general formula (XII) can be deprotonated with a strong base such as potassium tert-butoxide (KO-t-Bu) and subsequently reacted with an acylating compound of general formula R$_3$COL, wherein L represents a leaving group such as chloride, followed by treatment with an acid such as hydrochloric acid and the like. The resulting compound of general formula (XIII) can be reacted with an anhydride of general formula (R$_1$CO)$_2$O to give a compound of formula (XI).

Scheme 4:

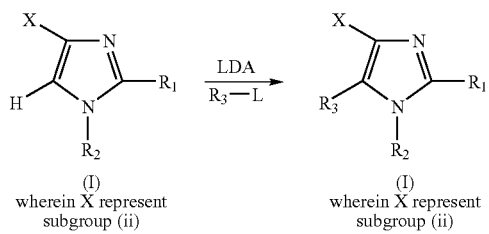

The symbols $R_1$–$R_3$ have the meanings as given above as given above on pages 2–5, X represents subgroup (ii).

A compound having general formula (I) wherein X represents subgroup (ii) and wherein the 5-position of the imidazole moiety contains a hydrogen atom can be deprotonated with a strong non-nucleophilic base such as lithium diisopropylamide (LDA), followed by treatment with a group R$_3$-L wherein L represents a leaving group to give a compound of general formula (I) wherein X represents subgroup (ii) and wherein the 5-position of the imidazole moiety contains a substituent R$_3$ (Scheme 4).

Scheme 5:

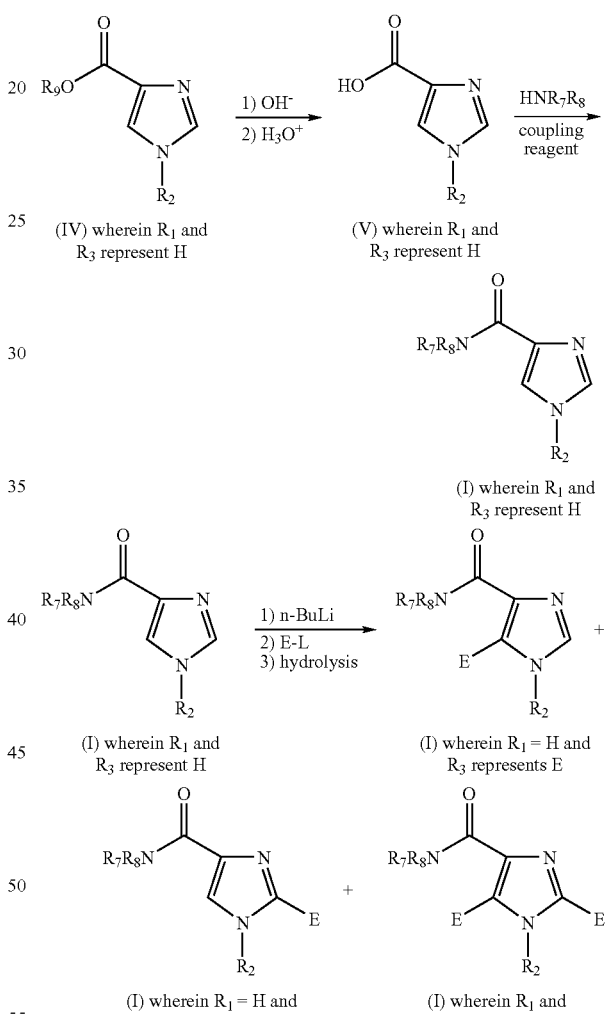

The symbols $R_2$, $R_7$, $R_8$ and $R_9$ have the meanings as given above as given above on pages 2–5, E is derived from an electrophilic moiety, L represents a leaving group.

An imidazole derivative of general formula (IV) wherein R$_1$ and R$_3$ represent hydrogen and wherein R$_9$ has the above-mentioned meaning can be converted via ester hydrolysis, for example by using lithium hydroxide (LiOH), NaOH, KOH or CsOH to provide intermediate imidazolecarboxylic acid alkali salts, which salts can be acidified by an acid such as aqueous hydrochloride (HCl) to give imidazolecarboxylic acid derivatives of general formula (V). Imidazolecarboxylic acid derivatives of general formula (V) can be amidated to give a compound of general formula (I) wherein $R_1$ and $R_3$ represent hydrogen and $R_2$, $R_7$ and $R_8$ have the abovementioned meaning. This compound of general formula (I) wherein $R_1$ and $R_3$ represent hydrogen and $R_2$, $R_7$ and $R_8$ have the abovementioned meaning can be deprotonated with a strong non-nucleophilic base such as lithium diisopropylamide (LDA) or n-Buli, followed by treatment with a group E-L wherein L represents a leaving group, such as iodide, bromide, or S-alkyl and E represents an electrophilic group, including but not limited to—S-alkyl, primary alkyl, chloro, bromo, iodo or cyano to give a compound of general formula (I) wherein X represents subgroup (ii) and wherein the 2/5-position of the imidazole moiety represent a substituent E and/or a hydrogen atom, depending on the type of group E-L applied in this reaction (Scheme 5). The definition of the group E is part of the definition of $R_1$ and $R_3$ and does not exceed the definitions of $R_1$ and $R_3$ given above. The mixtures of compounds that may be formed in the last reaction step in Scheme 5 can be separated and purified, for example by chromatographic methods or by crystallisation techniques.

Scheme 6:

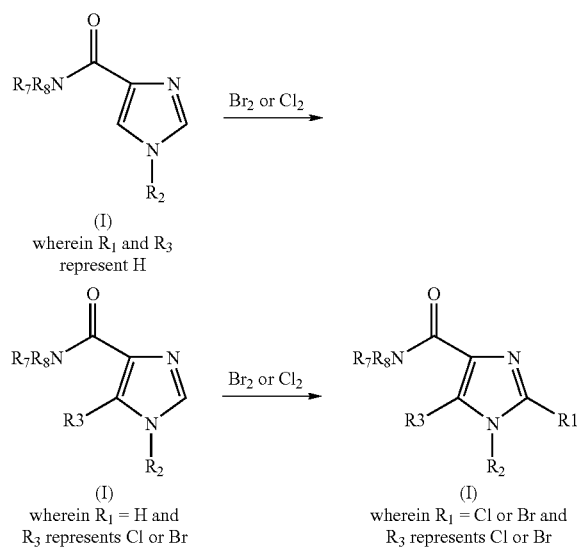

The symbols $R_2$, $R_7$, and $R_8$ have the meanings as given above as given above on pages 2–5.

A compound of general formula (I) wherein $R_1$ and $R_3$ represent hydrogen and $R_2$, $R_7$ and $R_8$ have the abovementioned meaning can be reacted with a halogenating agent such as N-chlorosuccinimide (NCS) or bromine ($Br_2$) in an inert organic solvent such as dichloromethane to give a compound of general formula (I) wherein $R_3$ represents Cl or Br and $R_1$ represents a hydrogen atom. A compound of general formula (I) wherein $R_3$ represents Cl or Br and $R_1$ represents a hydrogen atom can be reacted with a halogenating agent such as NCS or $Br_2$ in an inert organic solvent such as dichloromethane to give a compound of general formula (I) wherein $R_3$ represents Cl or Br and $R_1$ represents Cl or Br (Scheme 6).

For more detailed information on nucleophiles, electrophiles and the leaving group concept see: M. B. Smith and J. March: Advanced organic chemistry, p. 275, 5$^{th}$ ed., (2001) John Wiley & Sons, New York, ISBN: 0-471-58589-0). More information on addition and subsequent removal of protective groups in organic synthesis can be found in: T. W. Greene and P. G. M. Wuts, "Protective Groups in Organic Synthesis", third edition, John Wiley & Sons, Inc., New York, 1999.

Pharmaceutically acceptable salts may be obtained using standard procedures well known in the art, for example by mixing a compound of the present invention with a suitable acid, for instance an inorganic acid such as hydrochloric acid, or with an organic acid such as fumaric acid.

Pharmaceutical Preparations

The compounds of the invention can be brought into forms suitable for administration by means of usual processes using auxiliary substances such as liquid or solid carrier material. The pharmaceutical compositions of the invention may be administered enterally, orally, parenterally (intramuscularly or intravenously), rectally or locally (topically). They can be administered in the form of solutions, powders, tablets, capsules (including microcapsules), ointments (creams or gel) or suppositories. Suitable excipients for such formulations are the pharmaceutically customary liquid or solid fillers and extenders, solvents, emulsifiers, lubricants, flavorings, colorings and/or buffer substances. Frequently used auxiliary substances which may be mentioned are magnesium carbonate, titanium dioxide, lactose, mannitol and other sugars or sugar alcohols, talc, lactoprotein, gelatin, starch, cellulose and its derivatives, animal and vegetable oils such as fish liver oil, sunflower, groundnut or sesame oil, polyethylene glycol and solvents such as, for example, sterile water and mono- or polyhydric alcohols such as glycerol.

Compounds of the present invention are generally administered as pharmaceutical compositions which are important and novel embodiments of the invention because of the presence of the compounds, more particularly specific compounds disclosed herein. Types of pharmaceutical compositions that may be used include but are not limited to tablets, chewable tablets, capsules, solutions, parenteral solutions, suppositories, suspensions, and other types disclosed herein or apparent to a person skilled in the art from the specification and general knowledge in the art. In embodiments of the invention, a pharmaceutical pack or kit is provided comprising one or more containers filled with one or more of the ingredients of a pharmaceutical composition of the invention. Associated with such container(s) can be various written materials such as instructions for use, or a notice in the form prescribed by a governmental agency regulating the manufacture, use or sale of pharmaceuticals products, which notice reflects approval by the agency of manufacture, use, or sale for human or veterinary administration.

Pharmacological Methods

In vivo and in vitro pharmacological assays related to cannabinoid $CB_2$ receptor neurotransmission have been described in the literature. Some examples are:

Ibrahim, M. M. et al. (2003) *Proc. Natl. Acad. Sci. USA* 100, 10529-10533

Hanus, L. et al. (1999) *Proc. Natl. Acad. Sci. USA* 96, 14228-14233

Zhang, J. et al. (2003) *Eur. J. Neuroscience* 17, 2750-2754.

Klein, T. W. et al. (2003) *J. Leukoc. Biol.* 74, 486-496

Shoemaker, J. L. et al. (2005), *J. Pharmacol. Exp. Ther.* 315, 828-838

Iwamura, H. et al. (2001), *J. Pharmacol. Exp. Ther.* 296, 420-425.

In Vitro Affinity for Cannabinoid-$CB_1$ Receptors

The affinity of the compounds of the invention for cannabinoid $CB_1$ receptors can be determined using membrane preparations of Chinese hamster ovary (CHO) cells in which the human cannabinoid $CB_1$ receptor is stably transfected in conjunction with [$^3$H]CP-55,940 as radioligand. After incubation of a freshly prepared cell membrane preparation with the [³H]-ligand, with or without addition of compounds of the invention, separation of bound and free ligand is performed by filtration over glassfiber filters. Radioactivity on the filter is measured by liquid scintillation counting.

In Vitro Affinity for Cannabinoid-$CB_2$ Receptors

The affinity of the compounds of the invention for cannabinoid $CB_2$ receptors can be determined using membrane preparations of Chinese hamster ovary (CHO) cells in which the human cannabinoid $CB_2$ receptor is stably transfected in conjunction with [³H]CP-55,940 as radioligand. After incubation of a freshly prepared cell membrane preparation with the [³H]-ligand, with or without addition of compounds of the invention, separation of bound and free ligand is performed by filtration over glassfiber filters. Radioactivity on the filter is measured by liquid scintillation counting.

Due to their cannabinoid $CB_2$ receptor modulating activity the compounds according to the invention are suitable for use in the treatment of immune system disorders, inflammatory disorders, allergies, pain, neuropathic pain, multiple sclerosis, neurodegenerative disorders, dementia, dystonia, muscle spasticity, tremor, epilepsy, traumatic brain injury, stroke, Parkinson's disease, Alzheimer's disease, epilepsy, Huntington's disease, cerebral ischaemia, cerebral apoplexy, craniocerebral trauma, spinal cord injury, neuroinflammatory disorders, brainstem neurodegeneration, plaque sclerosis, viral encephalitis, demyelinisation related disorders, and other neurological disorders as well as in the treatment of cancers, diabetes, gastric diseases, lung diseases, asthma and cardiovascular diseases as well as other diseases wherein $CB_2$ receptor neurotransmission is involved.

The compounds of the invention can be brought into forms suitable for administration by means of usual processes using auxiliary substances and/or liquid or solid carrier materials.

Dose

The affinity of the compounds of the invention for cannabinoid $CB_2$ receptors was determined as described above. From the binding affinity measured for a given compound of formula (I), one can estimate a theoretical lowest effective dose. At a concentration of the compound equal to twice the measured $K_i$-value, 100% of the cannabinoid $CB_2$ receptors likely will be occupied by the compound. Converting that concentration to mg of compound per kg of patient yields a theoretical lowest effective dose, assuming ideal bioavailability. Pharmacokinetic, pharmacodynamic, and other considerations may alter the dose actually administered to a higher or lower value. The dosage expediently administered is 0.001-1000 mg/kg, such as 0.1-100 mg/kg of patient's bodyweight.

Treatment

The term "treatment" as used herein refers to any treatment of a mammalian, such as human condition or disease, and includes: (1) preventing the disease or condition from occurring in a subject which may be predisposed to the disease but has not yet been diagnosed as having it, (2) inhibiting the disease or condition, i.e., arresting its development, (3) relieving the disease or condition, i.e., causing regression of the condition, or (4) relieving the conditions caused by the disease, i.e., stopping the symptoms of the disease.

EXAMPLES

Example 1

Materials and Methods

All reactions involving moisture sensitive compounds or conditions were carried out under an anhydrous nitrogen atmosphere. Reactions were monitored by using thin-layer chromatography (TLC) on silica coated plastic sheets (Merck precoated silica gel 60 F254) with the indicated eluent. Spots were visualised by UV light (254 nm) or $I_2$. Flash chromatography refers to purification using the indicated eluent and Acros silica gel (0.030-0.075 mm). Petroleum ether means petroleum ether 40-60. Nuclear magnetic resonance spectra (¹H NMR and ¹³C NMR) were determined in the indicated solvent with tetramethylsilane as an internal standard. Chemical shifts are given in ppm (δ scale) downfield from tetra-methylsilane. Coupling constants J are given in hertz (Hz). Peakshapes in the NMR spectra are indicated with the symbols 'q' (quartet), 'dq' (double quartet), 't' (triplet), 'dt' (double triplet), 'd' (doublet), 'dd' (double doublet), 's' (singlet), 'br s' (broad singlet) and 'm' (multiplet). Melting points were recorded on a Büchi B-545 melting point apparatus or determined by a differential scanning calorimetry (DSC) method. Yields refer to isolated pure products.

Preparative LC/MS Instrumentation and Procedure

Sciex API 150 EX masspectrometer with electron spray,
2 Shimadzu LC8A LC pump,
Shimadzu SCL-10A VP system controller,
Shimadzu SPD-10A VP UV meter,
Gilson 215 injector/collector,
   Column: Phenomenex Luna C18 (2)
     : 150×21.2×5μ
   Eluant: A 100% Water+0.1% Formic acid on pH=3
     : B 100% Acetonitrile+0.1% Formic acid
   Injection: 2.5 ml
   Splitter: 1 to 50,000 with a make-up flow of 0.2 ml/min
     (25% $H_2O$/75% ACN met 0.25% HCOOH)
   MS scan: from 100-900 amu step 1 amu scan time 1 sec.
Method: Flow rates and gradient profiles.

| Total Time (min) | Flow rate (ml/min) | A % (v/v) | B % (v/v) |
| --- | --- | --- | --- |
| 0 | 5 | 95 | 5 |
| 2 | 5 | 95 | 5 |
| 2.1 | 20 | 95 | 5 |
| 12 | 20 | 0 | 100 |
| 14 | 20 | 0 | 100 |
| 14.5 | 20 | 95 | 5 |
| 15 | 20 | 95 | 5 |

Example 2

Syntheses of Specific Compounds

The specific compounds of which the synthesis is described below are intended to further illustrate the invention in more detail, and therefore are not deemed to restrict the scope of the invention in any way. Other embodiments of the invention will be apparent to those skilled in the art from consideration of the specification and practice of the invention disclosed herein. It is thus intended that the specification and compounds be considered as exemplary only, with a true scope and spirit of the invention being indicated by the claims.

Synthesis of Compound 1

Part A: A magnetically stirred mixture of ethyl 5-methyl-1H-imidazole-4-carboxylate (13.875 g, 0.090 mol), phenylboronic acid (13.16 g, 0.108 mol) and CuI (0.85 g, 0.0045 mol) in ethanol/water (900 ml, 1/1 (v/v)) was divided in 12 equal portions and reacted in parallel at 85° C. for 60 hours. After cooling to room temperature the 12 portions were combined and concentrated in vacuo. The residue was purified by flash chromatography (Ethylacetate/petroleum ether 40-65=1/1 (v/v)) to give ethyl 5-methyl-1-phenyl-1H-imidazole-4-carboxylate (5.88 g, 26% yield). $^1$H-NMR (400 MHz, CDCl$_3$): δ 1.42 (t, J=7 Hz, 3H), 2.47 (s, 3H), 4.40 (q, J=7 Hz, 2H), 7.26-7.31 (m 7.56 (m, 3H), 7.59 (s, 1H).

Part B: (−)-Cis-myrtanylamine (CAS 38235-68-6) (0.95 ml, 5.7 mmol) was dissolved in anhydrous dichloromethane (15 ml) and (CH$_3$)$_3$Al (2.9 ml of a 2 M solution in heptane, 5.8 mmol) was added. The resulting mixture was magnetically stirred for 10 minutes at room temperature and ethyl 5-methyl-1-phenyl-1H-imidazole-4-carboxylate (1.1 gram, 4.8 mmol) was added. The resulting mixture was stirred at 35° C. for 16 hours, poured into an aqueous NaHCO$_3$ solution, stirred for 30 minutes and filtered over hyflo. The filtrate was twice extracted with dichloromethane. The organic layers were dried over Na$_2$SO$_4$, filtered and concentrated in vacuo. Subsequent purification with flash chromatography (ethyl acetate/petroleum ether 40-65=1/2 (v/v)) gave N-[(1R,2S,5R)-rel-6,6-dimethylbicyclo[3.1.1]heptan-2-methyl]-5-methyl-1-phenyl-1H-imidazole-4-carboxamide, compound 1 (1.05 gram, 65% yield). Melting point: 85-89° C.

Compound 1

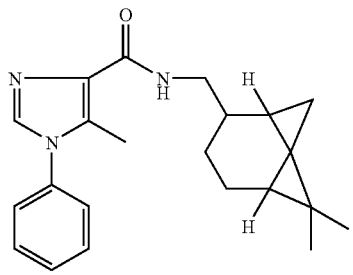

Analogously, the following compounds 2-7 were prepared:

Compound 2

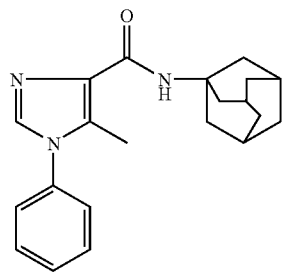

Compound 2: Melting point: 214-219° C.

Compound 3

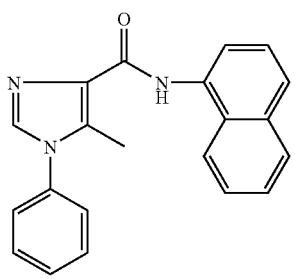

Compound 3: Melting point: 167-169° C.

Compound 4

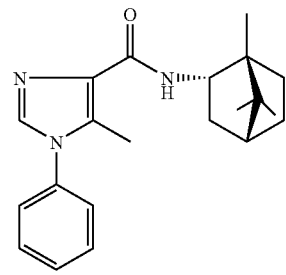

Compound 4: from R-(+)-bornylamine (CAS 32511-34-5). Melting point: 209-212° C.

Compound 5

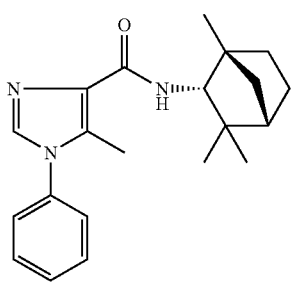

Compound 5: from endo-(1R)-1,3,3-trimethylbicyclo[2.2.1]heptan-2-amine. Melting point: 149-152° C.

Compound 6

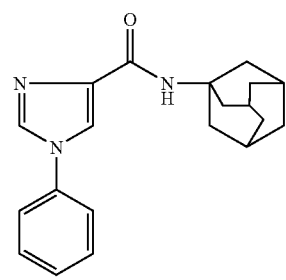

Compound 6: Melting point: 198-200° C.

Compound 7

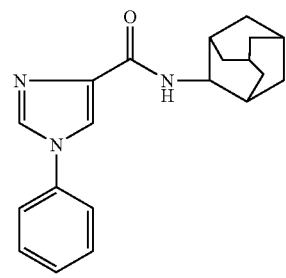

Compound 7: Melting point: 232-234° C.

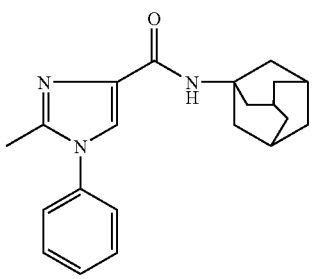

Compound 8

Synthesis of Compound 8

Part A: Ethyl 2-methyl-1-phenyl-1H-imidazole-4-carboxylate (4.8 gram, 21% yield) was prepared according to the procedure described (in J. Heterocyclic Chem. 1987, 24, 1757-1763) from ethyl 3-anilino-2-nitro-acrylate (23.6 gram, 0.01 mol) and triethylorthoacetate (150 ml). The initially formed crude product was purified by flash chromatography (eluent: diethyl ether). $R_f$ (diethylether~0.15) to give pure ethyl 2-methyl-1-phenyl-1H-imidazole-4-carboxylate as an oil.

Part B: Ethyl 2-methyl-1-phenyl-1H-imidazole-4-carboxylate (2.25 gram, 0.012 mol) was reacted (analogously to the procedure described hereinabove for compound 1) with AlMe$_3$ (7.2 ml of a 2M solution in hexane, 0.0144 mol) and 1-adamantane amine. HCl (2.25 g, 0.012 mol). The initially formed crude product was purified by flash chromatography (eluent: diethyl ether) to give N-adamantyl-2-methyl-1-phenyl-1H-imidazole-4-carboxamide (2.2 gram, 55% yield). Melting point: 207-210° C.

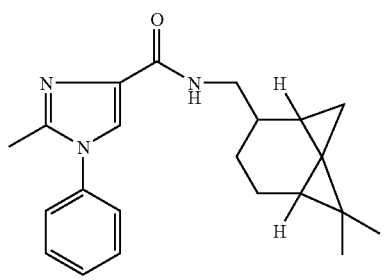

Compound 9

Compound 9 was prepared analogously to compound 6 from (−)-cis-myrtanylamine (CAS 38235-68-6). Melting point: 124-127° C.

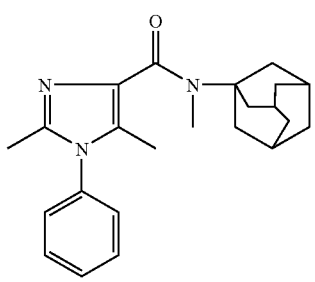

Compound 10

Compound 10: N-Adamantyl-2-methyl-1-phenyl-1H-imidazole-4-carboxamide (0.33 gram, 0.001 mol) was dissolved in anhydrous tetrahydrofuran (25 ml). The resulting solution was slowly added to a solution of lithium diisopropylamide (1.25 ml of a 2 M solution in heptane/THF, 0.0025 mol LDA) under N$_2$ at −70° C. A solution of methyl iodide (0.14 gram, 0.001 mol) in anhydrous THF was added and the resulting solution was stirred for 1 hour at −70° C. The solution was allowed to attain room temperature and stirred for another 2 hours and subsequently quenched with aqueous acetic acid. After concentration in vacuo the resulting residue was purified by flash chromatography (diethyl ether/petroleum ether (40-60)=3/1 (v/v)) to give compound 10 and compound 11, respectively.

Melting point compound 10: 180-183° C.

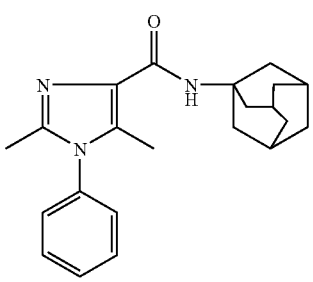

Compound 11

Compound 11: Compound 11 was prepared more efficiently by reacting ethyl 2,5-dimethyl-1-phenyl-1H-imidazole-4-carboxylate (Cf. the corresponding methyl ester 3j in J. Heterocyclic Chem. 1987, 24, 1757-1763) with AlMe$_3$ and 1-adamantane-amine. HCl, according to the Weinreb amidation procedure described hereinabove for compound 1, Part B.

Melting point: 201-204° C.

Synthesis of Compound 12

Part A: Ethyl 2,5-dimethyl-1-(3-methoxyphenyl)-1H-imidazole-4-carboxylate was prepared analogously to the procedure described (in J. Heterocyclic Chem. 1987, 24, 1757-1763) from ethyl 3-(3-methoxyphenylamino)-3-methyl-2-nitro-acrylate and triethylorthoacetate.

Part B: Ethyl 2,5-dimethyl-1-(3-methoxyphenyl)-1H-imidazole-4-carboxylate was amidated (analogously to the procedure described hereinabove for compound 1) (stirred at 70° C. for 16 hours) with AlMe$_3$ and (−)-cis-myrtanylamine (CAS 38235-68-6) to give compound 12. Melting point: 153-155° C.

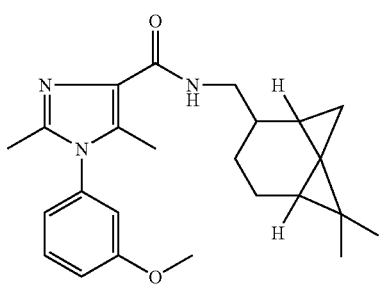

Compound 12

Analogously were prepared compounds 13-20.

Compound 13

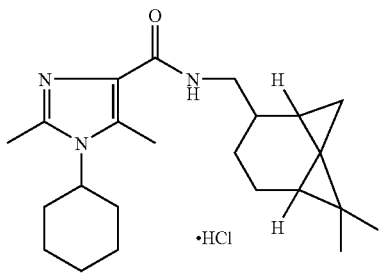

Compound 14

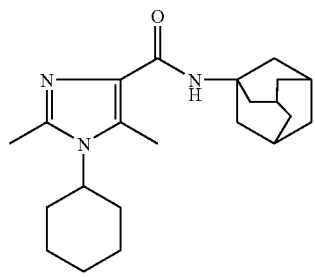

Compound 15

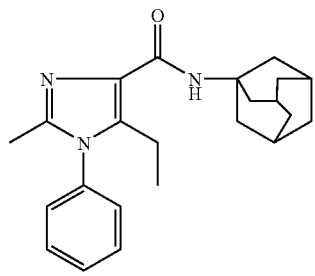

m.p.: 156-158° C. m.p.: 214-216° C. m.p.: 190-193° C.

Compound 16

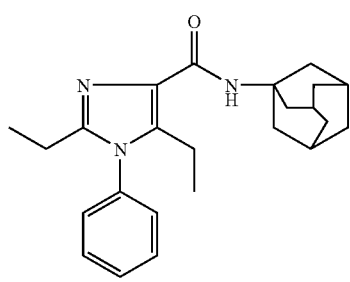

Compound 17

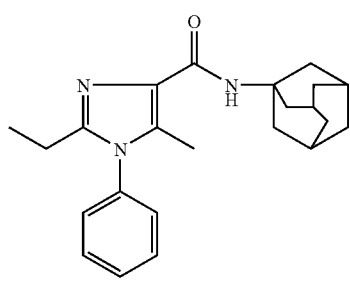

Compound 18

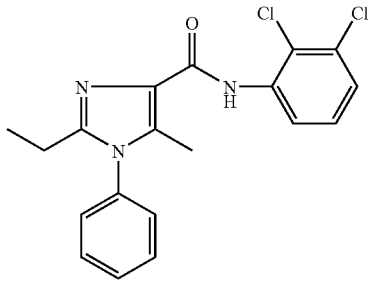

m.p.: 217-223° C. m.p.: 216-218° C. m.p.: 137-140° C.

Compound 19

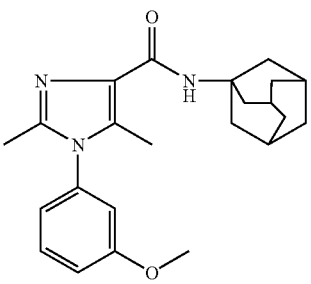

Compound 20 m.p.: 119-121° C. m.p.: 186-188° C.

Synthesis of Compound 21

Part A: To a magnetically stirred suspension of ethyl 4-methyl-1H-imidazole-5-carboxylate (15.42 gram, 0.100 mol) in anhydrous THF was slowly added sodium hydride (NaH) (4.88 g of a 60% suspension, 0.120 mol) and the resulting mixture was stirred at room temperature for 30 minutes. Benzyl bromide (13.8 ml, 0.120 mol) was slowly added and the resulting mixture was reacted for 16 hours. Water was added to the mixture. The organic layer was separated from the water layer. The water layer was extracted 3 times with ethylacetate. The organic layer was dried over $MgSO_4$, filtered and thoroughly concentrated to give an oil. The resulting residue was purified (in order to separate the two formed regioisomers) by flash chromatography (diethyl ether/ethyl acetate gradient) to give ethyl N-benzyl-5-methyl-1H-imidazole-4-carboxylate (11.4 gram, 47% yield). $^1$H-NMR (400 MHz, $CDCl_3$): δ 1.40 (t, J=7, 3H), 2.45 (s, 3H), 4.37 (q, J=7, 2H), 5.10 (s, 2H), 7.03-7.08 (m, 2H), 7.28-7.38 (m, 3H), 7.48 (s, 1H).

Part B: Ethyl N-benzyl-5-methyl-1H-imidazole-4-carboxylate (1.5 gram, 0.0061 mol) was reacted with adamantyl-1-amine. HCl (1.72 g, 0.0092 mol) and $Al(CH_3)_3$ (4.6 ml. 2M in hexane, 0.0092 mol) in 1,2-dichloroethane (20 ml) at 70° C. for 40 hours according to the procedure described for compound 1, part B. Purification by flash chromatography (ethyl acetate/petroleum ether=1/1 (v/v)) gave compound 21 (1.24 gram, 58%). Melting point: 182-184° C.

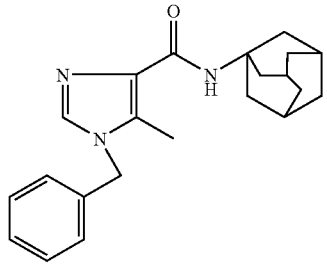

Compound 21

Analogously were prepared compounds 22-23:

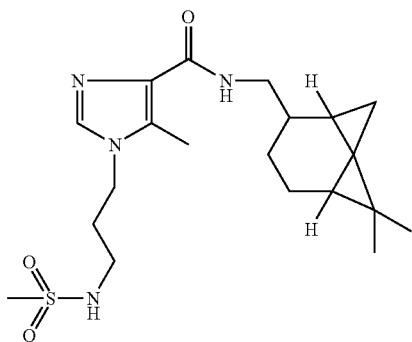

Compound 22

Synthesis of Compound 22

Compound 22 was prepared via the coupling of 3-(methylsulfonylamino)propyl chloride with ethyl 4-methyl-1H-imidazole-5-carboxylate using $K_2CO_3$ as the base in DMF at 90° C. for 20 hours, subsequent separation of the two formed regioisomers by flash chromatography (ethyl acetate/methanol=9/1 (v/v)), followed by the $Al(CH_3)_3$ catalyzed amidation with (−)-cis-myrtanylamine.

Compound 22. Melting point: 84-108° C. $R_f$ 0.35 (EtOAc/MeOH=4/1 (v/v)).

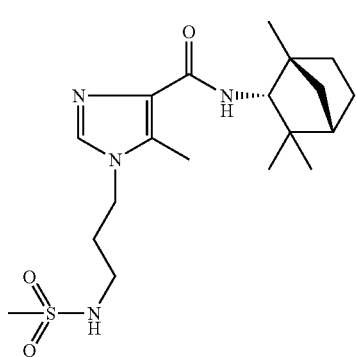

Compound 23

Compound 23 (from endo-(1R)-1,3,3-trimethylbicyclo[2.2.1]heptan-2-amine) Melting point: 149-156° C. $R_f$ 0.4 (EtOAc/MeOH=4/1 (v/v)).

Synthesis of Compound 24

Part A: To a magnetically stirred solution of ethyl N-benzyl-5-methyl-1H-imidazole-4-carboxylate (8.4 gram, 0.0345 mol) in methanol (200 ml) was slowly added a solution of KOH (7.3 gram, 85% grade, 0.110 mol) and the resulting mixture was heated at 80° C. for 2 hours. The solution was cooled to room temperature and concentrated HCl (9.2 ml) was subsequently added. The formed precipitate was collected by filtration to give N-benzyl-5-methyl-1H-imidazole-4-carboxylic acid (6.77 gram, 91% yield). Melting point: 292° C. (decomposition).

Part B: To a magnetically stirred solution of N-benzyl-5-methyl-1H-imidazole-4-carboxylic acid (6.77 gram, 0.031 mol) in anhydrous acetonitrile (35 ml) was successively added diisopropylethylamine (DIPEA) (17.2 ml, 0.0992 mol), HBTU (14.098 gram, 0.0372 mol) and methoxy-methylamine (3.63 gram, 0.0372 mol). The resulting mixture was reacted at 20° C. for 16 hours and subsequently concentrated in vacuo. The resulting residue was taken up in ethylacetate and successively washed with 5% aqueous $NaHCO_3$ solution and water. The organic layer was dried over $MgSO_4$, filtered and concentrated in vacuo. The resulting oily residue (18.45 gram) was purified by flash chromatography (ethyl acetate/acetone=7/3 (v/v)) to give N-methoxy-N-methyl-5-methyl-1-benzyl-1H-imidazole-4-carboxamide (10.77 gram, 82% yield). $MH^+$=260. $^1$H-NMR (400 MHz, $CDCl_3$): δ 2.34 (s, 3H), 3.47 (s, 3H), 3.77 (s, 3H), (s, 2H), 7.05-7.10 (m, 2H), 7.18-7.28 (m, 3H), 7.48 (s, 1H).

Part C: To a magnetically stirred solution of 1-naphtylmagnesium bromide (49 ml, 0.25 M in THF, 0.00123 mol) was added a solution of N-methoxy-N-methyl-5-methyl-1-benzyl-1H-imidazole-4-carboxamide (2.69 gram, 0.0104 mol) in anhydrous THF (10 ml) and the resulting solution was stirred for 1 hour. The reaction mixture was quenched in 1N HCl (21 ml) and subsequently extracted with ethyl acetate (EtOAc). The EtOAc layer was twice washed with water, dried over $MgSO_4$, filtered and concentrated in vacuo. The resulting crude residue was purified by flash chromatography (ethyl acetate/petroleum ether=1/1 (v/v)), followed by another flash chromatographic purification (dichloromethane/methanol=99/1 (v/v)) to give pure compound 24 (1.35 gram, 66% yield) as an oil. $^1$H-NMR (400 MHz, $CDCl_3$): δ 2.58 (s, 3H), 5.12 (s, 2H), 7.08-7.13 (m, 2H), 7.31-7.40 (m, 3H), 7.44-7.56 (m, 4H), 7.78-7.82 (m, 1H), 7.84-7.89 (m, 1H), 7.92-7.96 (m, 1H), 8.16-8.22 (m, 1H).

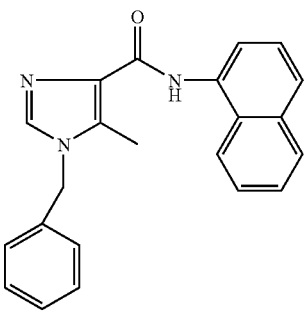

Compound 24

Synthesis of Compound 25

Analogously was prepared compound 25 (from N-methoxy-N-methyl-5-methyl-1-phenyl-1H-imidazole-4-carboxamide and n-hexyllithium in anhydrous diethyl ether). Flash chromatographic purification (methyl-tert-butyl ether/petroleum ether=1/3 (v/v)) of the initially isolated crude product gave compound 25 (24% yield) as a pale yellow oil.

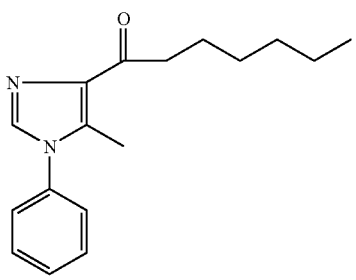

Compound 25

Compound 25. ¹H-NMR (400 MHz, CDCl₃): δ 0.86~0.94 (m, 3H), 1.25-1.47 (m, 6H), 1.70-1.80 (m, 2H), 2.50 (s, 3H), 3.04-3.11, (m, 2H), 7.26-7.32 (m, 2H), 7.50-7.59 (m, 4H).

Analogously was prepared compound 26

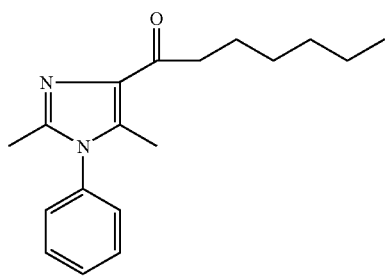

Compound 26

Compound 26; $R_f$(methanol/dichloromethane=3/97 (v/v), silica gel)=0.65.

Synthesis of Compound 27

To a magnetically stirred solution of N-(adamant-1-yl)-1-phenyl-1H-imidazole-4-carboxylate (1.61 gram, 0.005 mol) in dichloromethane (20 ml) was added a solution of Br₂ (0.52 ml, 0.010 mmol) in dichloromethane (5 ml). The resulting mixture was reacted at room temperature for 4 hours. Dichloromethane and 5% aqueous NaHCO₃ solution was added to the reaction mixture. The separated organic layer was dried over MgSO₄, filtered and concentrated in vacuo. The resulting residue was purified by flash chromatography (dichloromethane/acetone=19/1 (v/v)). Subsequent recrystallisation from acetonitrile gave N-(adamant-1-yl)-5-bromo-1-phenyl-1H-imidazole-4-carboxamide (0.51 gram, 26% yield). Melting point: 229-232° C.

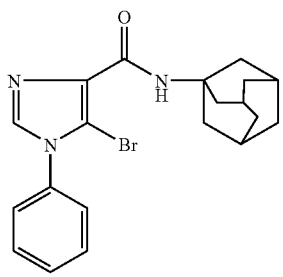

Compound 27

Analogously was prepared compound 28 in 17% yield using N-chlorosuccinimide (NCS) as the chlorinating agent for 40 hours at room temperature. Flash chromatography (dichloromethane/acetone=19/1 (v/v)). Melting point: 209-213° C.

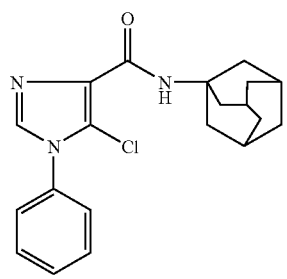

Compound 28

Synthesis of Compound 29

To a magnetically stirred solution of N-(adamant-1-yl)-5-bromo-1-phenyl-1H-imidazole-4-carboxylate (0.60 gram) in dichloromethane (20 ml) was added a solution of Br₂ (0.30 ml) in dichloromethane (5 ml) and triethylamine (0.21 ml). The resulting mixture was reacted at room temperature for 50 hours. Dichloromethane and 5% aqueous NaHCO₃ solution was added to the reaction mixture. The separated organic layer was dried over MgSO₄, filtered and concentrated in vacuo. The resulting residue was purified by flash chromatography (dichloromethane). Subsequent stirring in diethyl ether followed by filtration gave N-(adamant-1-yl)-2,5-dibromo-1-phenyl-1H-imidazole-4-carboxamide (0.29 gram). Melting point: 228-231° C.

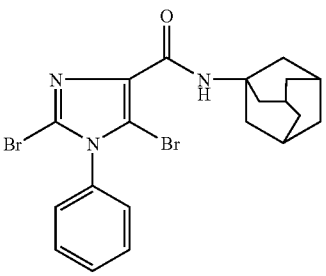

Compound 29

Analogously was prepared compound 30 in 32% yield from N-(adamant-1-yl)-5-chloro-1-phenyl-1H-imidazole-4-carboxylate using N-chlorosuccinimide (NCS) as the chlorinating agent. Melting point: 193-195° C.

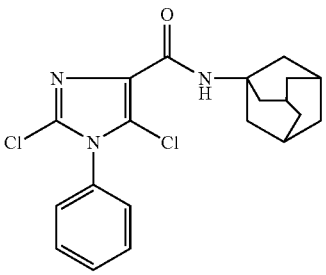

Compound 30

Synthesis of Compound 31

To a magnetically stirred suspension of N-(adamant-1-yl)-2-methyl-1-phenyl-1H-imidazole-4-carboxylate (2.01 gram, 0.006 mol) in anhydrous THF (20 ml) under N₂ at −70° C. was slowly added a solution of lithium diisopropylamide (LDA) (9.0 ml of a 2 M solution in heptane/THF, 0.018 mol LDA) under N₂ at −70° C. and the resulting solution was stirred for 1 hour. A solution of para-tolylsulfonyl cyanide (1.63 gram, 0.009 mol) in anhydrous THF (10 ml) was added and the resulting solution was stirred for 1 hour at −70° C. The solution was allowed to attain room temperature and stirred for another 12 hours and subsequently quenched with water. The mixture was extracted with diethyl ether. The organic layer is dried over MgSO₄, filtered and concentrated in vacuo. The resulting residue was purified by flash chromatography (dichloromethane/acetone=19/1 (v/v)) and subsequently recrystallized from acetonitrile to give compound 31 (0.23 gram, 11% yield). Melting point compound 30: 246-248° C.

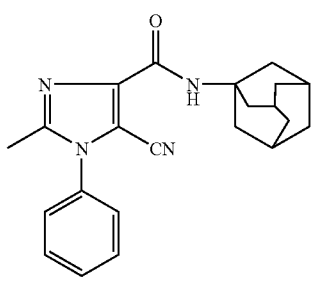

Compound 31

Analogously was prepared compound 32 in 31% yield from N-(adamant-1-yl)-2-methyl-1-phenyl-1H-imidazole-4-carboxylate using dimethyldisulfide(CH₃SSCH₃). Melting point: 172-173° C.

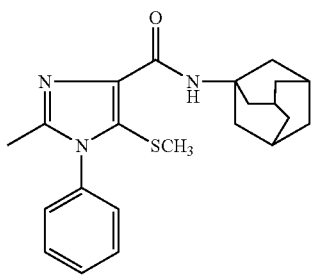

Compound 32

Analogously was prepared compound 33 in 28% yield from N-(adamant-1-yl)-2-methyl-1-phenyl-1H-imidazole-4-carboxylate using para-tolylsulfonyl chloride. Melting point: 216-218° C.

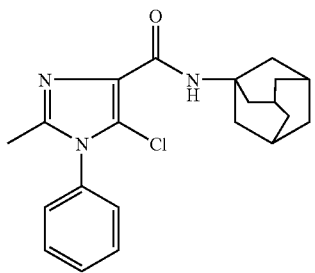

Compound 33

Analogously was prepared compound 33A from N-(adamant-1-yl)-2-methyl-1-phenyl-1H-imidazole-4-carboxylate using para-tolylsulfonyl bromide. Melting point: 242-244° C.

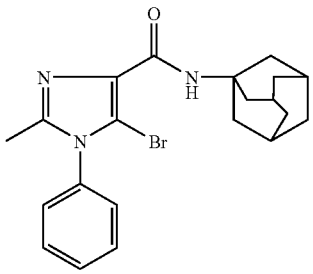

Compound 33A

Analogously was prepared compound 34 in 7% yield from N-(adamant-1-yl)-1-phenyl-1H-imidazole-4-carboxylate using para-tolylsulfonyl cyanide. Melting point: 237-239° C.

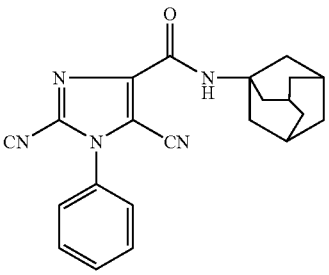

Compound 34

Analogously was prepared compound 35 in 12% yield from N-(adamant-1-yl)-1-phenyl-1H-imidazole-4-carboxylate using dimethyldisulfide(CH₃SSCH₃). Melting point: 166-168° C.

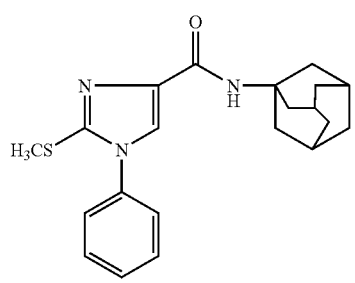

Compound 35

Synthesis of Compound 36

Part A: NaNO₂ (13.8 gram) was dissolved in water (48 ml) at 4° C. The resulting solution was slowly added to a magnetically stirred solution of 3-oxo-butyric acid methyl ester (17.4 gram, 0.15 mol) while keeping the temperature <5° C. After stirring the mixture for two hours water (120 ml) was added and the resulting mixture was extracted twice with diethyl ether. The combined organic layers were successively washed with water and a 5% aqueous NaHCO₃ solution. The organic layer was dried over MgSO₄, filtered and thoroughly concentrated to give crude 2-hydroxyimino-3-oxo-butyric acid methyl ester (24 gram) as a colorless oil which was not further purified. ¹H-NMR (400 MHz, CDCl₃): δ 2.42 (s, 3H), 3.91 (s, 3H), 9.90 (br s, 1H).

Part B: Crude 2-hydroxyimino-3-oxo-butyric acid methyl ester (24 gram, ~0.15 mol) dissolved in a magnetically stirred mixture of acetic acid (293 ml), acetic acid anhydride (110 ml) and Pd/C (4 gram) was hydrogenated for 20 hours at room temperature at 1 atmosphere H$_2$ pressure. After filtration over hyflo, the acetic acid and acetic acid anhydride were removed by concentration in vacuo. The resulting crude mixture was purified by flash chromatography (dichloromethane/methanol=95/5 (v/v)) to give 2-acetylamino-3-oxo-butyric acid methyl ester (16.7 gram, 60% yield) as a white solid. R$_f$ (dichloromethane/methanol=95/5 (v/v))=0.4. $^1$H-NMR (400 MHz, CDCl$_3$): δ 2.08 (s, 3H), 2.40 (s, 3H), 3.83 (s, 3H), 5.29 (d, J~7, 1H), 6.71 (br s, 1H).

Part C: To a magnetically stirred solution of 2-acetylamino-3-oxo-butyric acid methyl ester (5 gram, 28.9 mmol) in butyronitrile was added aniline (3.42 ml) and trifluoroacetic acid (2.89 ml) and the resulting mixture was heated at reflux for 45 minutes. The butyronitrile was removed in vacuo at room temperature and the resulting residues was taken up dichloromethane and washed twice with an aqueous potassium carbonate solution. The organic layer was dried over MgSO$_4$, filtered and concentrated in vacuo. The resulting residue was purified by flash chromatography (diethyl ether/acetone=4/1 (v/v)) to give methyl 2,5-dimethyl-1-phenyl-1H-imidazole-4-carboxylate (3.0 gram, 46% yield). $^1$H-NMR (400 MHz, CDCl$_3$): δ 2.22 (s, 3H), 2.33 (s, 3H), 3.91 (s, 3H), 7.18-7.22 (m, 2H), 7.51-7.59 (m, 3H).

Part D: To a magnetically stirred solution of methyl 2,5-dimethyl-1-phenyl-1H-imidazole-4-carboxylate (8.0 gram, 0.035 mol) in THF (100 ml) was added a solution of LiOH (1.68 gram) in water (100 ml). The resulting mixture was heated at 70° C. for 16 hours, allowed to attain room temperature and acidified with 2 molar equivalents of a 1N HCl solution. The formed precipitate was collected to give crude 2,5-dimethyl-1-phenyl-1H-imidazole-4-carboxylic acid (7.0 gram, 93% yield). $^1$H-NMR (400 MHz, DMSO-d$_6$): δ 2.31 (s, 3H), 2.43 (s, 3H), 7.56-7.61 (m, 2H), 7.66-7.71 (m, 3H).

Part D: To a magnetically stirred solution of 2,5-dimethyl-1-phenyl-1H-imidazole-4-carboxylic acid (0.6 gram, 0.0028 mol) in acetonitrile (35 ml) was successively added diisopropylethylamine (DIPEA, Hünig's base) (1.27 gram), O-benzotriazol-1-yl-N,N,N',N'-tetramethyluronium hexafluorophosphate (HBTU) (1.27 gram) and (−)-cis-myrtanylamine (1.05 ml, 0.0028 mol). The resulting mixture was reacted at 20° C. for 16 hours and subsequently concentrated in vacuo. The resulting residue was taken up in dichloromethane and washed with 5% aqueous NaHCO$_3$ solution. The organic layer was dried over MgSO$_4$, filtered and concentrated in vacuo. The resulting residue was purified by flash chromatography (dichoromethane/methanol=95/5 (v/v)) to give N-[(1R,2S,5R)-rel-6,6-dimethylbicyclo[3.1.1]heptan-2-methyl]-2,5-dimethyl-1-phenyl-1H-imidazole-4-carboxamide (compound 36) (0.70 gram, 72% yield). R$_f$ (silica gel/dichoromethane/methanol=95/5 (v/v))~0.6.

Compound 36

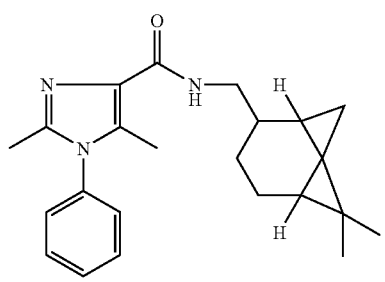

Analogously were prepared compounds 37-47:

Compound 37

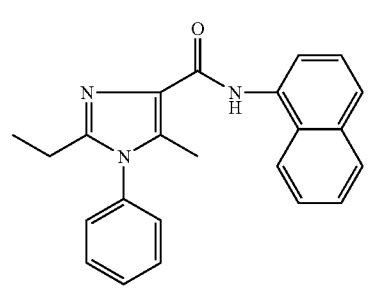

Compound 37: $^1$H-NMR (400 MHz, CDCl$_3$): δ 1.26 (t, J=7, 3H), 2.41 (s, 3H), 2.56 (q, J=7, 2H), 7.23-7.28 (m, 2H), 7.49-7.60 (m, 6H), 7.66 (d, J=8, 1H), 7.88 (d, J=8, 1H), 8.11 (d, J=8, 1H), 8.28 (d, J=8, 1H), 9.85 (s, 1H).

Compound 38

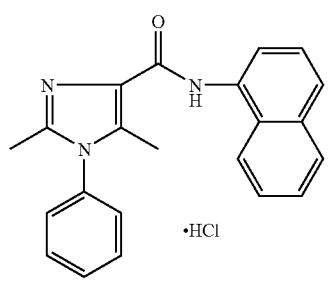

Compound 38: Melting point: 177-179° C.

Compound 39

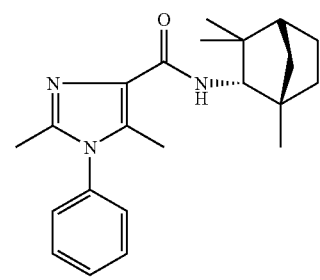

Compound 39: from endo-(1S)-1,3,3-trimethylbicyclo[2.2.1]heptan-2-amine. Melting point: 130-132° C. (DSC).

Compound 40

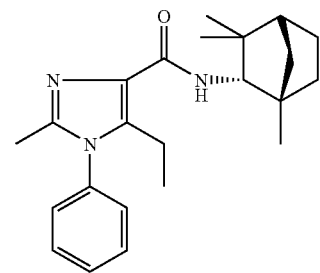

Compound 40: from endo-(1S)-1,3,3-trimethylbicyclo[2.2.1]heptan-2-amine. $^1$H-NMR (300 MHz, CDCl$_3$): δ 0.89 (s, 3H), 0.96 (t, J=7, 3H), 1.12 (s, 3H), 1.17-1.27 (m, 5H), 1.40-1.60 (m, 2H), 1.67-1.81 (m, 3H), 2.15 (s, 3H), 2.70-2.95 (m, 2H), 3.78 (dd, J~10 and 2, 1H), 7.18-7.23 (m, 2H), 7.34 (br d, J~10, 1H), 7.48-7.57 (m, 3H).

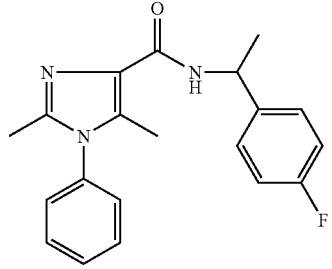

Compound 41

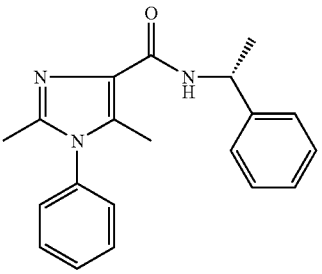

Compound 45

Compound 45: From R-(+)-phenethylamine.
$^{1}$H-NMR (300 MHz, CDCl$_{3}$): δ 1.58-1.61 (m, 3H), 2.17 (s, 3H), 2.33 (s, 3H), 5.25-5.35 (m, 1H), 7.15-7.54 (m, 11H).

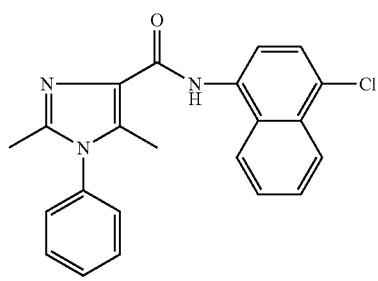

Compound 42

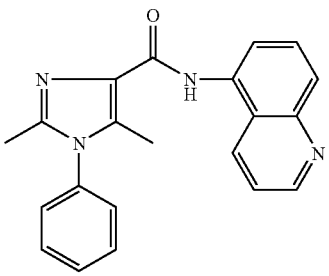

Compound 46

Compound 46: Melting point: 139-141° C. (DSC).

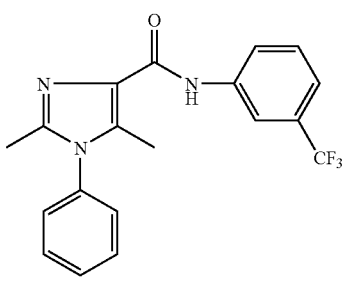

Compound 43

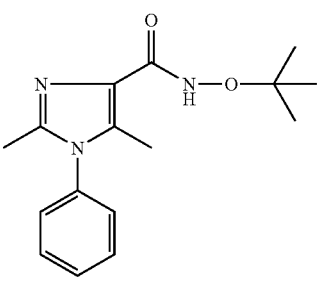

Compound 47 m.p.: 117.5-120° C. (DSC) m.p.: 193-196° C. (DSC) m.p.: 157-159° C. (DSC)

Compound 47: $^{1}$H-NMR (400 MHz, CDCl$_{3}$): δ 1.10 (s, 9H), 1.69 (s, 3H), 2.24 (s, 3H), 7.00-7.06 (m, 2H), 7.46-7.55 (m, 3H), the NH peak is invisible and probably merged with the H$_{2}$O peak at δ 1.60.

Synthesis of Compound 48

To a magnetically stirred solution of 2,5-dimethyl-1-phenyl-1H-imidazole-4-carboxylic acid (0.66 gram, 0.00306 mol) in dichloromethane (35 ml) was successively added diisopropylethylamine (DIPEA) (3.1 ml), CIP (2-chloro-1,3-dimethylimidazolinium hexafluorophosphate). (2.55 gram) and 3-hydroxyadamantane amine (0.612 gram, 0.00366 mol). The resulting mixture was reacted at 20° C. for 16 hours and subsequently concentrated in vacuo. The resulting residue was taken up in dichloromethane and washed with 5% aqueous NaHCO$_{3}$ solution. The organic layer was dried over MgSO$_{4}$, filtered and concentrated in vacuo. The resulting residue was purified by flash chromatography (dichoromethane/methanol=98/2 (v/v)) to give N-(3 hydroxy-adamant-1-yl)-2,5-dimethyl-1-phenyl-1H-imidazole-4-carboxamide (0.75 gram, 67% yield). R$_{f}$ (silica gel/dichoromethane/methanol=98/2 (v/v))~0.6. Melting point: 215-220° C.

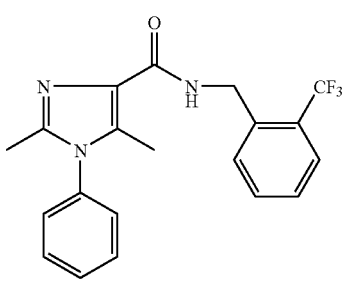

Compound 44

Compound 44: Melting point: 76-79° C. (DSC).

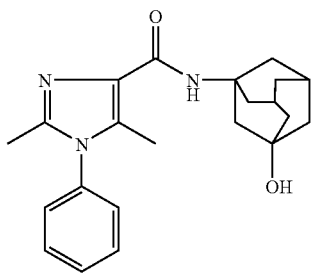
Compound 48
Analogously were prepared compounds 49-64:
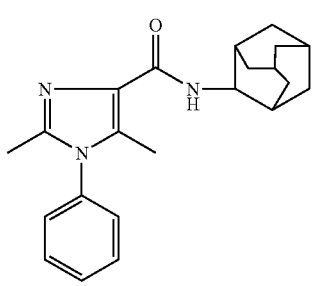
Compound 49
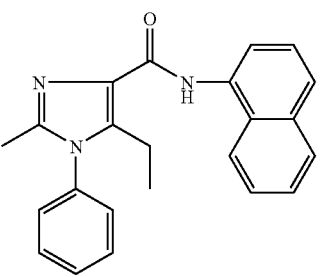
Compound 50
Compound 49: m.p.: 245-247° C. Compound 50: m.p.: 251-253° C.
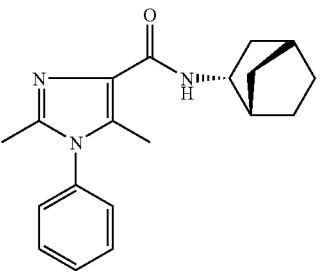
Compound 51
racemic, endo
Compound 51: (from racemic endo-2-amino-bicyclo[2.2.1]heptane: $^1$H-NMR (400 MHz, DMSO-$d_6$): δ 0.85-1.64 (m, 8H), 2.13 (s, 3H), 2.21 (br s, 1H), 2.24 (s, 3H), 2.40 (br s, 1H), 4.07-4.16 (m, 1H), 7.34 (br d, J~8, 2H), 7.40 (br d, J~7, 1H), 7.52-7.61 (m, 3H).
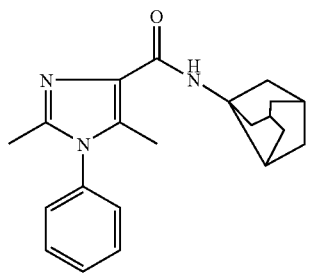
Compound 52
Compound 52: (from noradamantylamine): Melting point: 147-150° C.
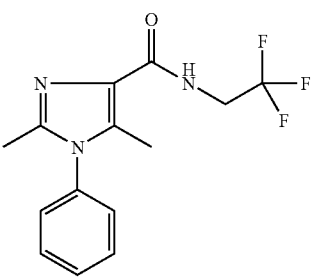
Compound 53
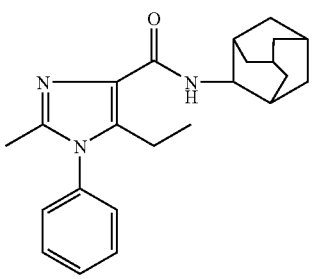
Compound 54
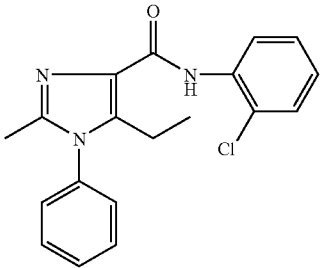
Compound 55
m.p.: 111-113° C. m.p.: 204-207° C. m.p.: 115-117° C.

Compound 56

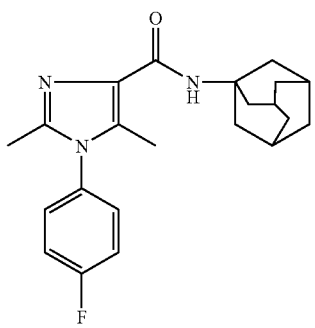

Compound 60

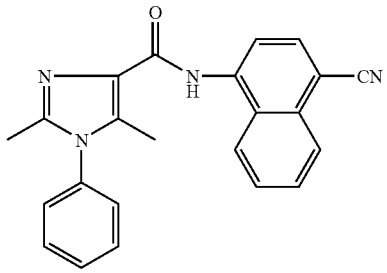

Compound 57

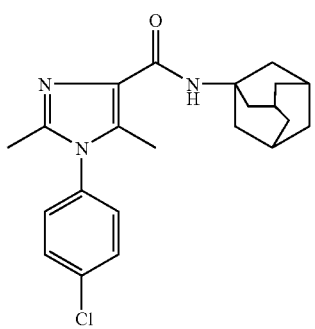

Compound 60: ¹H-NMR (300 MHz, CDCl$_3$): δ 2.29 (s, 3H), 2.43 (s, 3H), 7.23-7.27 (m, 2H), 7.54-7.60 (m, 3H), 7.70-7.76 (m, 2H), 7.95 (d, J=8 Hz, 1H), 8.17-8.21 (m, 1H), 8.27-8.29 (m, 1H), 8.63 (d, J=8 Hz, 1H), 10.20 (br s, 1H).
Melting point: 241.5° C. (DSC).

Compound 58

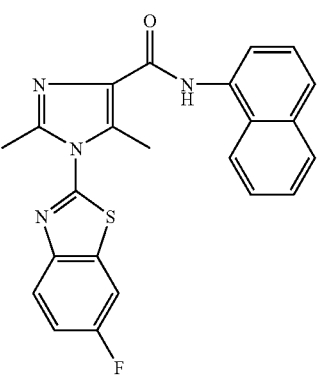

Compound 61

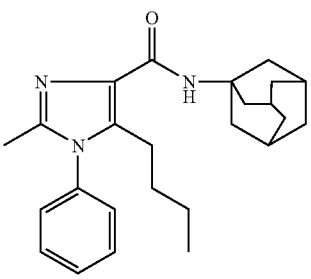

Compound 61: Melting point: 171-172° C.

m.p.: 208-210° C. m.p.: 243-245° C. m.p.: 178-181° C.

Compound 59

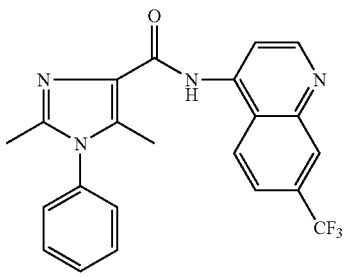

Compound 62

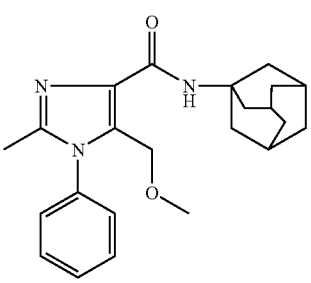

Compound 59: ¹H-NMR (300 MHz, CDCl$_3$): δ 2.28 (s, 3H), 2.43 (s, 3H), 7.23-7.27 (m, 2H), 7.55-7.60 (m, 3H), 7.79 (dd, J=9 and 2 Hz, 1H), 8.22 (d, J=9 Hz, 1H), 8.42 (s, 1H), 8.62 (d, J~5 Hz, 1H), 8.94 (d, J=5 Hz, 11H), 10.25 (brs, 1H).
Melting point: 198.5° C. (DSC).

Compound 62: Melting point: ~113° C. R$_f$ (diethyl ether/petroleum ether=1/1 (v/v)~0.15. ¹H-NMR (400 MHz, CDCl$_3$): δ 1.66-1.78 (m, 6H), 2.08-2.18 (m, 9H), 2.19 (s, 3H), 3.22 (s, 3H), 4.59 (s, 3H), 7.06 (br s, 1H), 7.25-7.30 (m, 2H), 7.47-7.55 (m, 3H).

Compound 63

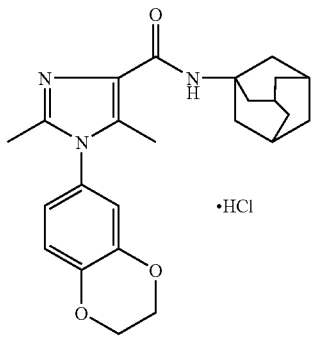

Compound 63: Melting point: 221-223° C.

Compound 64

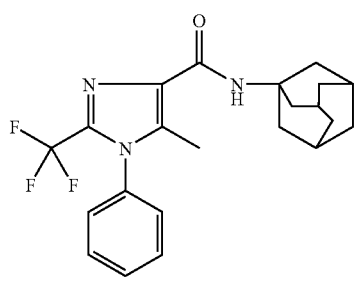

Compound 64: Melting point: 170-172° C.

Synthesis of Compound 65

Part A: To a magnetically stirred suspension of 2,5-dimethyl-1-phenyl-1H-imidazole-4-carboxylic acid (0.4 gram, 1.85 mmol) in $CHCl_3$ (4 ml) was added oxalyl chloride (0.34 gram, 2.685 mmol) and the resulting mixture was reacted at 58° C. for 2 hours and subsequently concentrated in vacuo. The resulting residue was taken up in dichloromethane and diisopropylethylamine (0.28 gram, 2.148 mmol) was subsequently added. A solution of 2,3-dichloroaniline (0.35 gram, 2.146 mmol) in dichloromethane (5 ml) was slowly added to the resulting mixture and the resulting mixture was reacted for 2 hours at room temperature and subsequently concentrated in vacuo. The resulting residue was purified by flash chromatography (dichloromethane) to give N-(2,3-dichlorophenyl)-2,5-dimethyl-1-phenyl-1H-imidazole-4-carboxamide (0.24 gram, 36% yield). Melting point: 127-129° C.

Compound 65

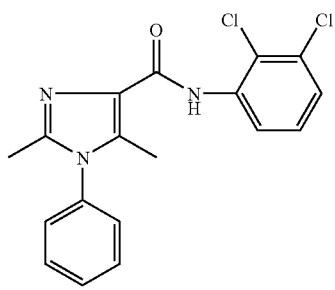

Analogously were prepared compounds 66-78:

Compound 66

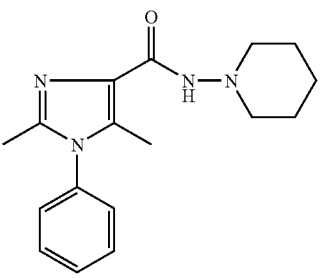

Compound 66: Melting point: 117-118° C.

Compound 67

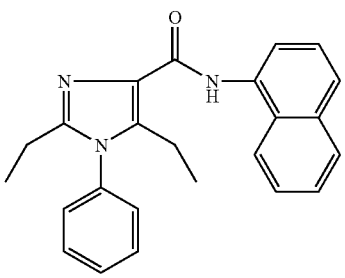

Compound 67: Melting point: 123-125° C.

Compound 68

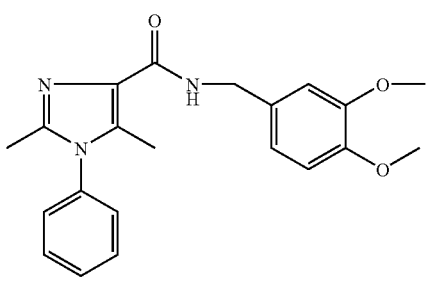

Compound 68: $^1$H-NMR (400 MHz, $CDCl_3$): δ 2.17 (s, 3H), 2.37 (s, 3H), 3.86 (s, 3H), 3.88 (s, 3H), 4.55 (d, J~6, 2H), 6.82 (d, J=8, 1H), 6.90-6.95 (m, 2H), 7.17-7.21 (m, 2H), 7.45 (br s, 1H), 7.50-7.57 (m, 3H).

Compound 69

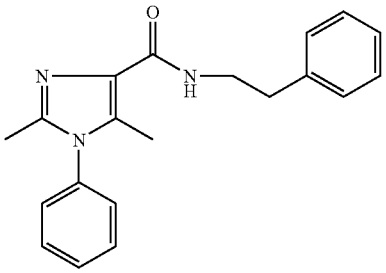

Compound 69: $^1$H-NMR (400 MHz, $CDCl_3$): δ 2.16 (s, 3H), 2.35 (s, 3H), 2.93 (t, J=7, 2H), 3.66 (q, J~7, 2H), 7.16-7.34 (m, 8H), 7.48-7.56 (m, 3H).

LC/MS: retention time: 3.13 minutes; $MH^+$=320.

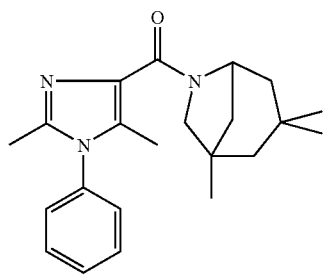

Compound 70

Compound 70: LC/MS: retention time: 2.67 minutes; MH$^+$=352.

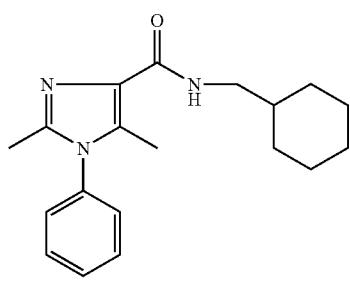

Compound 71

Compound 71: $^1$H-NMR (400 MHz, CDCl$_3$): δ 0.94-1.05 (m, 2H), 1.11-1.31 (m, 3H), 1.52-1.87 (m, 6H), 2.18 (s, 3H), 2.35 (s, 3H), 3.25 (t, J=7, 2H), 7.16-7.22-7.29 (m, 1H), 7.48-7.57 (m, 3H).
LC/MS: retention time: 2.76 minutes; MH$^+$=312.

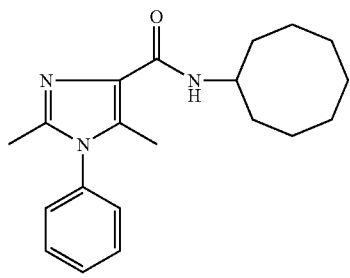

Compound 72

Compound 72: $^1$H-NMR (400 MHz, CDCl$_3$): δ 1.50-1.78 (m, 12H), 1.88-1.98 (m, 2H), 2.18 (s, 3H), 2.34 (s, 3H), 4.12-4.23 (m, 1H), 7.10-7.20 (m, 3H), 7.48-7.57 (m, 3H).
LC/MS: retention time: 2.88 minutes; MH$^+$=326.

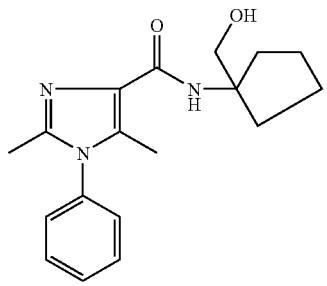

Compound 73

Compound 73: $^1$H-NMR (400 MHz, CDCl$_3$): δ 1.65-2.07 (m, 9H), 2.17 (s, 3H), 2.32 (s, 3H), 3.73 (s, 2H), 7.16-7.20 (m, 2H), 7.41 (br s, 1H), 7.49-7.57 (m, 3H).
LC/MS: retention time: 2.22 minutes; MH$^+$=314.

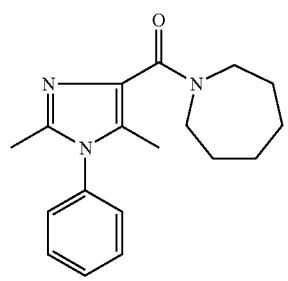

Compound 74

Compound 74: $^1$H-NMR (400 MHz, CDCl$_3$): δ 1.56-1.66 (m, 4H), 1.73-1.87 (m, 4H), 2.18 (br s, 6H), 3.65 (t, J=7, 2H), 3.91 (t, J=7, 2H), 7.19-7.23 (m, 2H), 7.47-7.56 (m, 3H).
LC/MS: retention time: 2.12 minutes; MH$^+$=297.

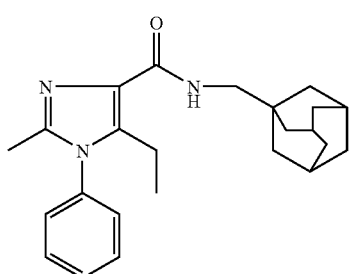

Compound 75 fumaric acid

Compound 75: R$_f$ (dichloromethane/methanol=95/5 (v/v))=0.65.

Compound 76

(structure)

Compound 76: LC/MS: retention time: 1.88 minutes; MH$^+$=307.

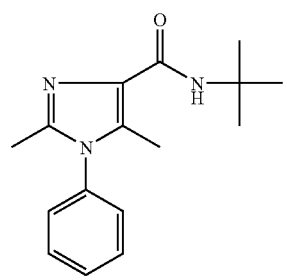

Compound 77 m.p.: 134–135° C.

-continued

Compound 78

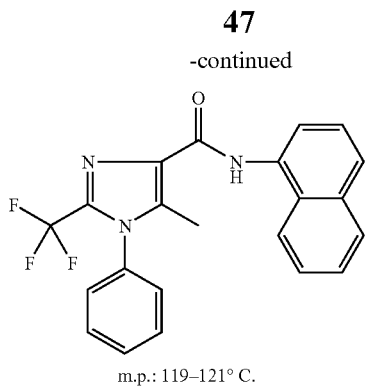

m.p.: 119–121° C.

Example 3

Formulation of Compound 1

For oral (p.o.) administration: To the desired quantity (0.5-5 mg) of the solid compound 1 in a glass tube, some glass beads were added and the solid was milled by vortexing for 2 minutes. After addition of 1 ml of a solution of 1% methylcellulose in water and 2% (v/v) of Poloxamer 188 (Lutrol F68), the compound was suspended by vortexing for 10 minutes. The pH was adjusted to 7 with a few drops of aqueous NaOH (0.1N). Remaining particles in the suspension were further suspended by using an ultrasonic bath.

For intraperitoneal (i.p.) administration: To the desired quantity (0.5-15 mg) of the solid compound 1 in a glass tube, some glass beads were added and the solid was milled by vortexing for 2 minutes. After addition of 1 ml of a solution of 1% methylcellulose and 5% mannitol in water, the compound was suspended by vortexing for 10 minutes. Finally the pH was adjusted to 7.

Example 4

Pharmacological Test Results

Cannabinoid receptor affinity data obtained according to the protocols given above are shown in the table below. BMS-I, BMS-II and BMS-III are the three exemplified imidazoles in WO 01/58869 (examples 64, 65 and 66 therein, respectively). These three specific imidazole derivatives all contain a L-phenylalanine derived carboxamide moiety at the 4-position of their (1H)-imidazole moiety as shown below. Our invention includes novel 1H-imidazole derivatives which lack such a L-phenylalanine derived carboxamide moiety but have approximately hundred-fold higher $CB_2$ receptor affinities as compared to the prior art compounds exemplified in WO 01/58869 as becomes clear from the data depicted in Table 1.

BMS-I

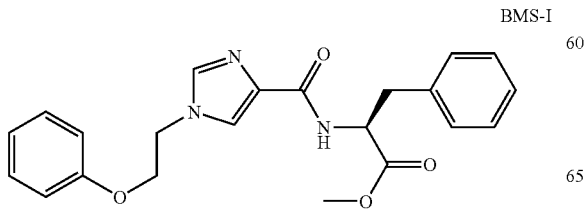

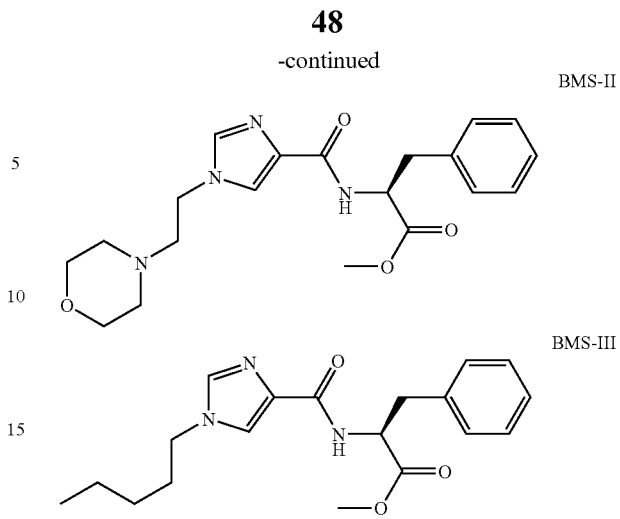

BMS-II

BMS-III

TABLE 1

| Compound | Human cannabinoid-$CB_1$ receptor In vitro affinity - $pK_i$ | Human cannabinoid-$CB_2$ receptor In vitro affinity - $pK_i$ value |
| --- | --- | --- |
| BMS-I | — | 6.4 |
| BMS-II | — | <6.0 |
| BMS-III | — | 7.2 |
| Compound 1 | <6.0 | 7.3 |
| Compound 11 | <6.0 | 9.0 |
| Compound 14 | <6.0 | 8.2 |
| Compound 15 | 6.2 | >9.0 |
| Compound 20 | 6.6 | 8.0 |
| Compound 26 | — | 6.8 |
| Compound 33 | — | 8.1 |
| Compound 33A | 6.1 | 8.2 |
| Compound 44 | — | 8.8 |
| Compound 49 | <6.0 | 8.6 |
| Compound 72 | — | 8.3 |

— = not determined

The invention claimed is:

1. A compound of formula (I)

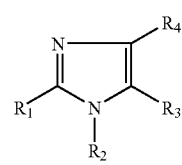

(I)

or a tautomer, a stereoisomer, or N-oxides thereof, or a pharmacologically acceptable salt, hydrate, or solvate of any of the foregoing, wherein:

$R_1$ is chosen from: hydrogen; halogen; $C_{1-3}$-alkyl optionally substituted with at least one substituent chosen from 1-3 fluorine atoms, hydroxy, and amino; $C_{2-3}$-alkynyl or $C_{2-3}$-alkenyl, wherein the $C_{2-3}$-alkynyl and $C_{2-3}$-alkenyl are optionally substituted with 1-3 fluorine atoms; acetyl; cyclopropyl; cyano; methylsulfonyl; ethylsulfonyl; methylsulfinyl; ethylsulfinyl; trifluoromethylsulfanyl; methylsulfanyl; ethylsulfanyl; formyl; and $C_{2-4}$-heteroalkyl having at least one heteroatom chosen from nitrogen, oxygen, and sulfur, $R_2$ is chosen from:
phenyl optionally substituted with 1, 2, 3, 4 or 5 substituents Y, which can be the same or different, and is chosen from methyl, ethyl, propyl, methoxy, ethoxy, hydroxy, trifluoromethyl, trifluoromethoxy, carbamoyl, phenyl and cyano,
heteroaryl having at least one heteroatom chosen from nitrogen, oxygen, and sulfur, which is optionally substituted with 1, 2 or 3 substituents Y, as defined above;
mono-unsaturated and fully saturated 4-10 membered monocyclic, fused bicyclic and fused tricyclic carbocyclic ring systems;
mono-unsaturated and fully saturated 4-10 membered monocyclic, fused bicyclic and fused tricyclic heterocyclic ring systems having at least one heteroatom chosen from nitrogen, oxygen, and sulfur, which carbocyclic and heterocyclic ring systems are optionally substituted with 1-5 substituents chosen from methyl, ethyl, amino, hydroxy, and fluoro;
a group of formula $CH_2$—$R_5$, wherein $R_5$ is chosen from: phenyl substituted with 1, 2, 3, 4 or 5 substituents Y as defined above; heteroaryl having at least one heteroatom chosen from nitrogen, oxygen, and sulfur, and 1,2,3,4-tetrahydronaphthyl, and indanyl, wherein the heteroaryl, 1,2,3,4-tetrahydronaphtyl, and indanyl are optionally substituted with 1, 2 or 3 substituents Y as defined above; mono-unsaturated and fully saturated monocyclic, fused bicyclic and fused tricyclic 4-10 membered carbocyclic ring systems; mono-unsaturated and fully saturated 4-10 membered monocyclic, fused bicyclic and fused tricyclic heterocyclic ring systems having at least one heteroatom chosen from nitrogen, oxygen, and sulfur, wherein the carbocyclic and heterocyclic ring systems are optionally substituted with 1-5 substituents chosen from methyl, ethyl, amino, hydroxy, and fluoro; and
methylsulfonylaminoalkyl; methylsulfonylalkyl; and acetamidoalkyl,
with the proviso that $R_2$ is not 6-methyl-2-pyridyl, a quinolin-2-one group substituted with a methyl group, or a biphenyl group, and when $R_2$ is a group of formula $CH_2$—$R_5$, $R_1$ is hydrogen, $R_3$ is an optionally substituted phenyl, hydrogen, halogen, optionally substituted $C_1$-$C_8$ alkyl, $C_3$-$C_8$ cycloalkyl, optionally substituted $C_5$-$C_8$-heterocycloalkyl having at least one heteroatom chosen from nitrogen, oxygen, and sulfur, optionally substituted heteroaryl having at least one heteroatom chosen from nitrogen, oxygen, and sulfur, or optionally substituted benzyl, $R_4$ is formula (ii), and $R_7$ is $C_1$-$C_4$ alkyl, $R_5$ is not a phenyl group substituted with 1-3 substituents chosen from methyl, ethyl, propyl, methoxy, ethoxy, trifluoromethyl, trifluoromethoxy, and cyano;
$R_3$ is chosen from: hydrogen; halogen; formyl; $C_{1-6}$-alkylsulfonyl; $C_{1-6}$-alkylsulfinyl; $C_{1-6}$-alkylsulfanyl; trifluoromethylsulfanyl; benzylsulfanyl; cyano; $C_{1-8}$-alkyl optionally substituted with 1-5 substituents chosen from fluoro, hydroxy, and amino; $C_{2-6}$-alkynyl, $C_{2-6}$-alkenyl, $C_{1-6}$-alkanoyl, $C_{3-8}$-cycloalkyl, $C_{5-8}$-heterocycloalkyl having at least one heteroatom chosen from nitrogen, oxygen, and sulfur, and $C_{2-6}$-heteroalkyl having at least one heteroatom chosen from nitrogen, oxygen, and sulfur, wherein the $C_{2-6}$-alkynyl, $C_{2-6}$-alkenyl, $C_{1-6}$-alkanoyl, $C_{3-8}$-cycloalkyl, $C_{5-8}$-heterocycloalkyl, and $C_{2-6}$-heteroalkyl are optionally substituted with at least one substituent chosen from 1-3 methyl groups, ethyl, amino, hydroxy, and 1-3 fluorine atoms; phenyl optionally substituted with 1-5 substituents Y, as defined above; heteroaryl having at least one heteroatom chosen from nitrogen, oxygen, and sulfur optionally substituted with 1, 2 or 3 substituents Y, as defined above; benzyl and heteroarylmethyl having at least one heteroatom chosen from nitrogen, oxygen, and sulfur, wherein the benzyl and heteroarylmethyl are optionally substituted with 1, 2 or 3 substituents Y, as defined above,
$R_4$ is chosen from formula (i) and formula (ii) wherein:

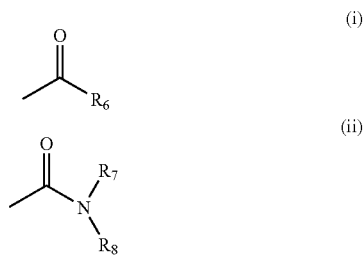

$R_6$ is chosen from: $C_{4-8}$ branched and linear alkyl, $C_{3-8}$ cycloalkyl, $C_{3-8}$-cycloalkyl-$C_{1-2}$-alkyl, $C_{5-7}$-heterocycloalkyl-$C_{1-2}$-alkyl having at least one heteroatom chosen from nitrogen, oxygen, and sulfur, $C_{5-10}$-bicycloalkyl, $C_{5-10}$-bicycloalkyl-$C_{1-2}$-alkyl, $C_{5-10}$-heterobicycloalkyl-$C_{1-2}$-alkyl having at least one heteroatom chosen from nitrogen, oxygen, and sulfur, $C_{6-10}$-tricycloalkyl, $C_{6-10}$-tricycloalkyl-$C_{1-2}$-alkyl, and $C_{6-10}$-heterotricycloalkyl-$C_{1-2}$-alkyl having at least one heteroatom chosen from nitrogen, oxygen, and sulfur, which groups are each optionally substituted with 1-5 substituents chosen from methyl, hydroxy, ethyl, trifluoromethyl, and fluoro; and phenyl, benzyl, naphthyl, and phenethyl, wherein the phenyl, benzyl, naphthyl, and phenethyl are optionally substituted on their aromatic ring system with 1-3 substituents Y as defined above, with the proviso that $R_6$ is not a 2-methylphenyl;
$R_7$ is chosen from: hydrogen; $C_{1-6}$ linear alkyl optionally substituted with 1-3 fluorine atoms; and isopropyl;
$R_8$ is chosen from: $C_{2-6}$ alkyl substituted with at least one substituent chosen from hydroxy, amino, and 1-3 fluorine atoms; $C_{7-10}$ branched alkyl; $C_{3-8}$ cycloalkyl, $C_{5-8}$ heterocycloalkyl having at least one heteroatom chosen from nitrogen, oxygen, and sulfur, $C_{3-8}$-cycloalkyl-$C_{1-2}$-alkyl, $C_{5-7}$-heterocycloalkyl-$C_{1-2}$-alkyl having at least one heteroatom chosen from nitrogen, oxygen, and sulfur, $C_{5-10}$-bicycloalkyl, $C_{5-10}$-bicycloalkyl-$C_{1-2}$-alkyl, $C_{5-10}$-heterobicycloalkyl-$C_{1-2}$-alkyl having at least one heteroatom chosen from nitrogen, oxygen, and sulfur, $C_{6-10}$-tricycloalkyl, $C_{6-10}$-tricycloalkyl-$C_{1-2}$-alkyl, $C_{6-10}$-heterotricycloalkyl-$C_{1-2}$-alkyl having at least one heteroatom chosen from nitrogen, oxygen, and sulfur, which groups are optionally substituted with 1-5 substituents chosen from methyl, hydroxy, ethyl, amino, hydroxymethyl, trifluoromethyl, and fluoro; phenyl substituted with 1-5 substituents Y as defined above; naphthyl, 1,2,3,4-tetrahydronaphthyl, and indanyl, which naphthyl, 1,2,3,4-tetrahydronaphthyl, and indanyl groups are optionally substituted with 1-3 substituents Y as defined above; phenyl-$C_{1-3}$-alkyl and diphenyl-$C_{1-3}$-alkyl, which groups are optionally substituted on their phenyl ring with 1-5 substituents Y as defined above; benzyl substituted with 1-5 substituents Y as defined above; heteroaryl having at least one heteroatom chosen from nitrogen, oxygen, and sulfur, heteroarylmethyl having at least one heteroatom chosen from nitrogen, oxygen, and sulfur, naphthylmethyl, heteroarylethyl having at least one heteroatom chosen from nitrogen, oxygen, and sulfur, which heteroaryl, heteroarylmethyl, naphthylmethyl, and heteroarylethyl groups are optionally substituted with 1-3 substituents Y as defined above; piperidinyl; azepanyl; morpholinyl; azabicyclo[3.3.0] octanyl; 4-hydroxypiperidinyl; and pyrrolidinyl, with the proviso that $R_8$ is not 6-methoxy-benzothiazol-2-yl, or a pyrrolidinyl group substituted with an amino group;

or $R_7$ and $R_8$, together with the nitrogen atom to which they are bonded, form a saturated or unsaturated, nonaromatic or partly aromatic monocyclic, bicyclic or tricyclic heterocyclic group optionally having at least one additional heteroatom chosen from nitrogen, oxygen, and sulfur having 7 to 10 ring atoms, which saturated or unsaturated, nonaromatic or partly aromatic monocyclic, bicyclic or tricyclic heterocyclic group is optionally substituted with 1-5 substituents chosen from $C_{1-3}$ alkyl, hydroxy, methoxy, cyano, phenyl, trifluoromethyl, and halogen;

or $R_7$ and $R_8$, together with the nitrogen atom to which they are bonded, form a saturated monocyclic heterocyclic group, having 5 to 6 ring atoms and optionally having at least one additional heteroatom chosen from nitrogen, oxygen, and sulfur, which heterocyclic group is substituted with 1-5 substituents chosen from $C_{1-3}$ alkyl, hydroxy, amino, phenyl, benzyl, and fluoro, with the proviso that $R_7$ and $R_8$, together with the nitrogen atom to which they are bonded, do not form a trimethyl-substituted aza-bicyclo[3.2.1]octanylgroup, or a pyrrolidinyl group substituted with an amino group.

2. The compound according to claim 1, wherein:
$R_1$ is chosen from: halogen; $C_{1-3}$-alkyl optionally substituted with at least one group chosen from 1-3 fluorine atoms, hydroxy, and amino; $C_{2-3}$-alkynyl and $C_{2-3}$-alkenyl, which $C_{2-3}$-alkynyl and $C_{2-3}$-alkenyl are optionally substituted with 1-3 fluorine atoms; acetyl; cyclopropyl; cyano; methylsulfonyl; ethylsulfonyl; methylsulfinyl; ethylsulfinyl; trifluoromethylsulfanyl; methylsulfanyl; ethylsulfanyl; formyl; and $C_{2-4}$-heteroalkyl; and $R_2$, $R_3$, and $R_4$ are as defined in claim 1.

3. The compound according to claim 1, wherein:
$R_3$ is chosen from: hydrogen; halogen; formyl; methylsulfonyl; ethylsulfonyl; methylsulfinyl; ethylsulfinyl; trifluoromethylsulfanyl; methylsulfanyl; ethylsulfanyl; cyano; $C_{1-6}$-alkyl optionally substituted with at least one substituent chosen from 1-3 fluorine atoms, hydroxy, and amino; $C_{2-6}$-alkynyl, $C_{2-6}$-alkenyl, $C_{1-6}$-alkanoyl, $C_{3-8}$-cycloalkyl, $C_{5-8}$-heterocycloalkyl having at least one heteroatom chosen from nitrogen, oxygen, and sulfur, $C_{2-6}$-heteroalkyl having at least one heteroatom chosen from nitrogen, oxygen, and sulfur, wherein the $C_{2-6}$-alkynyl, $C_{2-6}$-alkenyl, $C_{1-6}$-alkanoyl, $C_{3-8}$-cycloalkyl, $C_{5-8}$-heterocycloalkyl, and $C_{2-6}$-heteroalkyl are optionally substituted with at least one substituent chosen from 1-3 methyl groups, ethyl, amino, hydroxy, and 1-3 fluorine atoms; phenyl optionally substituted with 1-5 substituents Y, as in claim 1; heteroaryls having at least one heteroatom chosen from nitrogen, oxygen, and sulfur optionally substituted with 1, 2 or 3 substituents Y, as defined in claim 1; benzyl and heteroarylmethyl wherein the benzyl and heteroarylmethyl are optionally substituted with 1, 2 or 3 substituents Y, as defined in claim 1;

$R_4$ has the formula (ii)

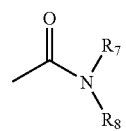

(ii)

wherein
$R_7$ is chosen from: hydrogen; $C_{1-6}$ linear alkyl; and isopropyl;
$R_8$ is chosen from: $C_{2-8}$ alkyl substituted with at least one substituent chosen from hydroxy, amino, and 1-3 fluorine atoms; $C_{7-10}$ branched alkyl; $C_{3-8}$ cycloalkyl; $C_{5-8}$ heterocycloalkyl having at least one heteroatom chosen from nitrogen, oxygen, and sulfur, $C_{3-8}$-cycloalkyl-$C_{1-2}$-alkyl, $C_{5-7}$-heterocycloalkyl-$C_{1-2}$-alkyl having at least one heteroatom chosen from nitrogen, oxygen, and sulfur, $C_{5-10}$ bicycloalkyl, $C_{5-10}$-bicycloalkyl-$C_{1-2}$-alkyl, $C_{5-10}$-heterobicycloalkyl-$C_{1-2}$-alkyl, $C_{6-10}$ tricycloalkyl, $C_{6-10}$-tricycloalkyl-$C_{1-2}$-alkyl, $C_{6-10}$heterotricycloalkyl-$C_{1-2}$-alkyl having at least one heteroatom chosen from nitrogen, oxygen, and sulfur, which groups are optionally substituted with 1-5 substituents chosen from methyl, hydroxy, ethyl, amino, hydroxymethyl, trifluoromethyl, and fluoro; phenyl substituted with 1-5 substituents Y as defined in claim 1; naphthyl, 1,2,3,4-tetrahydronaphthyl, and indanyl, which groups are optionally substituted with 1-3 substituents Y, as defined in claim 1; phenyl-$C_{1-3}$-alkyl and diphenyl-$C_{1-3}$-alkyl, which groups are optionally substituted on their phenyl ring with 1-5 substituents Y, as defined in claim 1; benzyl substituted with 1-5 substituents Y, as defined in claim 1; heteroaryl having at least one heteroatom chosen from nitrogen, oxygen, and sulfur, heteroarylmethyl having at least one heteroatom chosen from nitrogen, oxygen, and sulfur, heteroarylethyl having at least one heteroatom chosen from nitrogen, oxygen, and sulfur, which heteroaryl, heteroarylmethyl, and heteroarylethyl group are optionally substituted with 1-3 substituents Y, as defined in claim 1; piperidinyl; azepanyl; morpholinyl; azabicyclo[3.3.0]octanyl; 4-hydroxypiperidinyl; and pyrrolidinyl, with the proviso that $R_8$ is not 6-methoxy-benzothiazol-2-yl or a pyrrolidinyl group substituted with an amino group;

or $R_7$ and $R_8$, together with the nitrogen atom to which they are bonded, form a saturated or unsaturated, nonaromatic or partly aromatic, monocyclic, bicyclic or tricyclic heterocyclic group optionally having at least one additional heteroatom chosen from nitrogen, oxygen, and sulfur having 7 to 10 ring atoms, which heterocyclic group is optionally substituted with at least one substituent chosen from one or two $C_{1-3}$ alkyl groups, hydroxy, phenyl, trifluoromethyl and halogen or $R_7$ and $R_8$, together with the nitrogen atom to which they are bonded, form a saturated monocyclic heterocyclic group, having 5 to 6 ring atoms and optionally having at least one additional heteroatom chosen from nitrogen, oxygen, and sulfur, which heterocyclic group is substituted with at least one substituent chosen from 1-3 $C_{1-3}$ alkyl groups, hydroxy, and 1-2 fluoro atoms,
with the proviso that $R_7$ and $R_8$, together with the nitrogen atom to which they are bonded, do not form a trimethyl-substituted aza-bicyclo[3.2.1]octanyl, or a pyrrolidinyl group substituted with an amino group.

4. The compound according to claim 1, wherein:

$R_1$ is chosen from: halogen and $C_{1-3}$-alkyl optionally substituted with at least substituent chosen from 1-3 fluorine atoms and hydroxy; $C_{2-3}$-alkynyl; $C_{2-3}$-alkenyl; acetyl; cyclopropyl; cyano, methylsulfonyl; methylsulfinyl; methylsulfanyl; and $C_{2-4}$-heteroalkyl having at least one heteroatom chosen from nitrogen, oxygen, and sulfur;

$R_2$ is chosen from:
  phenyl optionally substituted with 1, 2, 3, 4 or 5 substituents Y as defined in claim 1; monocyclic heteroaryl having at least one heteroatom chosen from nitrogen, oxygen, and sulfur and being optionally substituted with 1, 2 or 3 substituents Y, as defined in claim 1;
  mono-unsaturated and fully saturated 4-10 membered monocyclic, fused bicyclic or fused tricyclic carbocyclic ring systems and mono-unsaturated and fully saturated 4-10 membered monocyclic, fused bicyclic and fused tricyclic heterocyclic having at least one heteroatom chosen from nitrogen, oxygen, and sulfur ring systems, which carbocyclic and heterocyclic ring systems are optionally substituted with 1-5 substituents chosen from methyl, ethyl, amino, hydroxy, and fluoro;
  a group of formula $CH_2$—$R_5$ wherein $R_5$ is chosen from phenyl substituted with 1, 2, 3, 4 or 5 substituents Y as defined in claim 1; heteroaryl having at least one heteroatom chosen from nitrogen, oxygen, and sulfur, 1,2,3,4-tetrahydronaphthyl, and indanyl, which heteroaryl, 1,2,3,4-tetrahydronaphthyl, and indanyl are optionally substituted with 1, 2 or 3 substituents Y as defined in claim 1; mono-unsaturated and fully saturated monocyclic, fused bicyclic and fused tricyclic 4-10 membered carbocyclic ring systems, mono-unsaturated and fully saturated 4-10 membered monocyclic, fused bicyclic and fused tricyclic heterocyclic ring systems, which carbocyclic and heterocyclic rings systems having at least one heteroatom chosen from nitrogen, oxygen, and sulfur are optionally substituted with 1-3 methyl groups, ethyl, amino, hydroxy, and fluoro,
  with the proviso that $R_2$ is not 6-methyl-2-pyridyl, a quinolin-2-one group substituted with a methyl group, or a biphenyl group, and when $R_2$ is a group of formula $CH_2$—$R_5$, $R_1$ is hydrogen, $R_3$ is an optionally substituted phenyl, hydrogen, halogen, optionally substituted $C_1$-$C_8$ alkyl, $C_3$-$C_8$ cycloalkyl, optionally substituted $C_5$-$C_8$-heterocycloalkyl having at least one heteroatom chosen from nitrogen, oxygen, and sulfur, optionally substituted heteroaryl having at least one heteroatom chosen from nitrogen, oxygen, and sulfur, or optionally substituted benzyl, $R_4$ is formula (ii), and $R_7$ is $C_1$-$C_3$ linear alkyl, $R_5$ is not a phenyl group substituted with 1-3 substituents chosen from methyl, ethyl, propyl, methoxy, ethoxy, trifluoromethyl, trifluoromethoxy, and cyano;

$R_3$ is chosen from hydrogen; halogen; methylsulfanyl; cyano; $C_{1-6}$-alkyl optionally substituted with at least one substituent chosen from 1-3 fluorine atoms, hydroxy, and amino; $C_{2-6}$-alkynyl and $C_{2-6}$-alkenyl, which groups are optionally substituted with 1-3 fluorine atoms;

$R_4$ has the formula (ii)

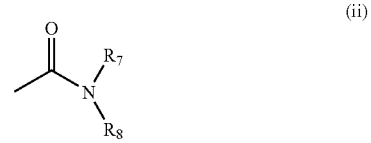

wherein
$R_7$ is chosen from hydrogen and $C_{1-3}$ linear alkyl;
$R_5$ is chosen from: $C_{2-6}$ alkyl substituted with at least one substituent chosen from hydroxy, amino, and 1-3 fluorine atoms; $C_{7-10}$ branched alkyl, $C_{3-8}$ cycloalkyl, $C_{5-8}$ heterocycloalkyl having at least one heteroatom chosen from nitrogen, oxygen, and sulfur, $C_{3-8}$-cycloalkyl-$C_{1-2}$-alkyl, $C_{5-7}$-heterocycloalkyl-$C_{1-2}$-alkyl having at least one heteroatom chosen from nitrogen, oxygen, and sulfur, $C_{5-10}$ bicycloalkyl, $C_{5-10}$-bicycloalkyl-$C_{1-2}$-alkyl, $C_{5-10}$-heterobicycloalkyl-$C_{1-2}$-alkyl having at least one heteroatom chosen from nitrogen, oxygen, and sulfur, $C_{6-10}$ tricycloalkyl, $C_{6-10}$-tricycloalkyl-$C_{1-2}$-alkyl, and $C_{6-10}$-heterotricycloalkyl-$C_{1-2}$-alkyl having at least one heteroatom chosen from nitrogen, oxygen, and sulfur, which groups are optionally substituted with 1-5 substituents chosen from methyl, hydroxy, ethyl, amino, hydroxymethyl, trifluoromethyl, and fluoro; phenyl substituted with 1-5 substituents Y as defined in claim 1; naphthyl, 1,2,3,4-tetrahydronaphthyl, and indanyl, which groups are optionally substituted with 1-3 substituents Y, as defined in claim 1; phenyl-$C_{1-3}$-alkyl, and diphenyl-$C_{1-3}$-alkyl, which groups are optionally substituted on their phenyl ring with 1-5 substituents Y, as defined in claim 1; benzyl substituted with 1-5 substituents Y as defined in claim 1; heteroaryl having at least one heteroatom chosen from nitrogen, oxygen, and sulfur, heteroarylmethyl having at least one heteroatom chosen from nitrogen, oxygen, and sulfur, and heteroarylethyl having at least one heteroatom chosen from nitrogen, oxygen, and sulfur, which heteroaryl, heteroarylmethyl, and heteroarylethyl are optionally substituted with 1-3 substituents Y, as defined in claim 1; piperidinyl; azepanyl; morpholinyl; azabicyclo[3.3.0]octanyl; 4-hydroxypiperidinyl; and pyrrolidinyl, with the proviso that $R_8$ is not 6-methoxy-benzothiazol-2-yl, or a pyrrolidinyl group substituted with an amino group.

5. A compound of formula (I)

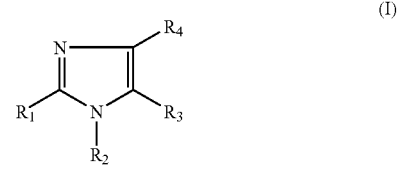

or a tautomer, a stereoisomer, or N-oxides thereof, or a pharmacologically acceptable salt, hydrate, or solvate of any of the foregoing, wherein:

$R_1$ is chosen from: halogen; $C_{1-3}$-alkyl optionally substituted with at least one substituent chosen from 1-3 fluoro atoms and hydroxy; cyano; and methylsulfanyl;

$R_2$ is chosen from: mono-unsaturated and fully saturated 5-7 membered monocyclic carbocyclic ring systems substituted with 1-5 substituents chosen from methyl, ethyl, amino, hydroxyl, and fluoro; phenyl optionally substituted with 1, 2, 3, 4 or 5 substituents Y, which can be the same or different, and chosen from methyl, ethyl, propyl, methoxy, ethoxy, hydroxy, trifluoromethyl, trifluoromethoxy, carbamoyl, phenyl and cyano;

$R_3$ is chosen from: hydrogen; halogen; methylsulfanyl; cyano; $C_{1-6}$-alkyl optionally substituted with at least one substituent chosen from 1-3 fluorine atoms, hydroxyl, and amino;

$R_4$ has the formula (ii)

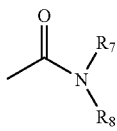

(ii)

wherein
$R_7$ is chosen from hydrogen and methyl;
$R_8$ is chosen from: $C_{2-6}$ alkyl substituted with 1-3 fluoro atoms; $C_{7-10}$ branched alkyl, $C_{3-8}$ cycloalkyl, $C_{5-8}$ heterocycloalkyl having at least one heteroatom chosen from nitrogen, oxygen, and sulfur, $C_{3-8}$-cycloalkyl-$C_{1-2}$-alkyl, $C_{5-7}$-heterocycloalkyl-$C_{1-2}$-alkyl having at least one heteroatom chosen from nitrogen, oxygen, and sulfur, $C_{5-10}$-bicycloalkyl, $C_{5-10}$-bicycloalkyl-$C_{1-2}$-alkyl, $C_{5-10}$-heterobicycloalkyl-$C_{1-2}$-alkyl having at least one heteroatom chosen from nitrogen, oxygen, and sulfur, $C_{6-10}$ tricycloalkyl, $C_{6-10}$-tricycloalkyl-$C_{1-2}$-alkyl, and $C_{6-10}$-heterotricycloalkyl-$C_{1-2}$-alkyl having at least one heteroatom chosen from nitrogen, oxygen, and sulfur, which groups are optionally substituted with 1-5 substituents chosen from methyl, hydroxy, ethyl, amino, hydroxymethyl, trifluoromethyl, and fluoro; phenyl group substituted with 1-5 substituents Y which can be the same or different, and chosen from methyl, ethyl, propyl, methoxy, ethoxy, hydroxy, trifluoromethyl, trifluoromethoxy, carbamoyl, phenyl and cyano; naphthyl, 1,2,3,4-tetrahydronaphthyl, and indanyl, which groups are optionally substituted with 1-3 substituents Y, which can be the same or different, and chosen from methyl, ethyl, propyl, methoxy, ethoxy, hydroxy, trifluoromethyl, trifluoromethoxy, carbamoyl, phenyl and cyano; phenyl-$C_{1-3}$-alkyl and diphenyl-$C_{1-3}$-alkyl, which groups are optionally substituted on their phenyl ring with 1-5 substituents Y which can be the same or different, and chosen from methyl, ethyl, propyl, methoxy, ethoxy, hydroxy, trifluoromethyl, trifluoromethoxy, carbamoyl, phenyl and cyano; benzyl substituted with 1-5 substituents Y which can be the same or different, and chosen from methyl, ethyl, propyl, methoxy, ethoxy, hydroxy, trifluoromethyl, trifluoromethoxy, carbamoyl, phenyl and cyano; and heteroaryl, heteroarylmethyl, and heteroarylethyl having at least one heteroatom chosen from nitrogen, oxygen, and sulfur, which groups are optionally substituted with 1-3 substituents Y, which can be the same or different, and chosen from methyl, ethyl, propyl, methoxy, ethoxy, hydroxy, trifluoromethyl, trifluoromethoxy, carbamoyl, phenyl and cyano, with the proviso that $R_8$ is not 6-methoxy-benzothiazol-2-yl or a pyrrolidinyl group substituted with an amino group.

6. A compound of formula (I)

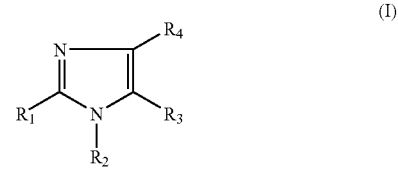

(I)

or a tautomer, a stereoisomer, or N-oxides thereof, or a pharmacologically acceptable salt, hydrate, or solvate of any of the foregoing, wherein:

$R_1$ is chosen: from halogen and $C_{1-2}$-alkyl optionally substituted with 1-3 fluoro atoms; cyano; and methylsulfanyl;

$R_2$ is chosen from: saturated six-membered monocyclic carbocyclic rings; and phenyl optionally substituted with 1, 2 or 3 substituents Y, which can be the same or different, and chosen from methyl, ethyl, propyl, methoxy, ethoxy, hydroxy, trifluoromethyl, trifluoromethoxy, carbamoyl, phenyl and cyano;

$R_3$ is chosen from: hydrogen; halogen; methylsulfanyl; cyano; and $C_{1-4}$-alkyl optionally substituted with 1-3 fluoro atoms, $R_4$ has the formula (ii)

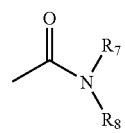

(ii)

wherein
$R_7$ is chosen from hydrogen and methyl;
$R_8$ is chosen from: $C_{2-6}$ alkyl substituted with 1-3 fluoro atoms; $C_{7-10}$ branched alkyl, $C_{3-8}$ cycloalkyl, $C_{5-8}$ heterocycloalkyl having at least one heteroatom chosen from nitrogen, oxygen, and sulfur, $C_{3-8}$-cycloalkyl-$C_{1-2}$-alkyl, $C_{5-7}$-heterocycloalkyl-$C_{1-2}$-alkyl having at least one heteroatom chosen from nitrogen, oxygen, and sulfur, $C_{5-10}$ bicycloalkyl, $C_{5-10}$-bicycloalkyl-$C_{1-2}$-alkyl, $C_{5-10}$-heterobicycloalkyl-$C_{1-2}$-alkyl having at least one heteroatom chosen from nitrogen, oxygen, and sulfur, $C_{6-10}$ tricycloalkyl, $C_{6-10}$-tricycloalkyl-$C_{1-2}$-alkyl, and $C_{6-10}$-heterotricycloalkyl-$C_{1-2}$-alkyl having at least one heteroatom chosen from nitrogen, oxygen, and sulfur, which groups are optionally substituted with 1-5 substituents chosen from methyl, hydroxy, ethyl, amino, hydroxymethyl, trifluoromethyl, and fluoro; phenyl substituted with 1-3 substituents Y which can be the same or different, and chosen from methyl, ethyl, propyl, methoxy, ethoxy, hydroxy, trifluoromethyl, trifluoromethoxy, carbamoyl, phenyl and cyano; naphthyl optionally substituted with 1-3 substituents Y which can be the same or different, and chosen from methyl, ethyl, propyl, methoxy, ethoxy, hydroxy, trifluoromethyl, trifluoromethoxy, carbamoyl, phenyl and cyano; phenyl-$C_{1-2}$-alkyl optionally substituted on the phenyl ring with 1-3 substituents Y which can be the same or different, and chosen from methyl, ethyl, propyl, methoxy, ethoxy, hydroxy, trifluoromethyl, trifluoromethoxy, carbamoyl, phenyl and cyano; and benzyl substituted with 1-5 substituents Y which can be the same or different, and chosen from methyl, ethyl, propyl, methoxy, ethoxy, hydroxy, trifluoromethyl, trifluoromethoxy, carbamoyl, phenyl and cyano.

7. A pharmaceutical composition comprising:
- a therapeutically effective amount of at least one compound of formula (I) according to claim 1, or a tautomer, a stereoisomer, or N-oxides thereof, or a pharmacologically acceptable salt, hydrate, or solvate of any of the foregoing; and
- at least one additional ingredient chosen from pharmaceutically acceptable carriers and pharmaceutically acceptable auxiliary substances.

8. A method of preparing a pharmaceutical composition according to claim 7, comprising:
- combining the at least one compound of formula (I), or a tautomer, a stereoisomer, or N-oxides thereof, or a pharmacologically acceptable salt, hydrate, or solvate of any of the foregoing, with the at least one additional ingredient chosen from pharmaceutically acceptable carriers and pharmaceutically acceptable auxiliary substances, and providing the pharmaceutical composition in a form suitable for administration.

\* \* \* \* \*

UNITED STATES PATENT AND TRADEMARK OFFICE
CERTIFICATE OF CORRECTION

Page 1 of 1

PATENT NO. : 8,937,184 B2
APPLICATION NO. : 11/353155
DATED : January 20, 2015
INVENTOR(S) : Lange et al.

It is certified that error appears in the above-identified patent and that said Letters Patent is hereby corrected as shown below:

On the Title Page, Item (54), and in the Specification, column 1, line 2, in the Title, "CB2" should read --$CB_2$--.

On the Title Page, Item (73), in the Assignee, "Abbvie" should read --AbbVie--.

In the Claims

In claim 1, column 49, line 25, "1,2,3,4-tetrahydronaphtyl," should read --1,2,3,4-tetrahydronaphthyl,--.

In claim 3, column 52, line 14, "$C_{2-8}$ alkyl" should read --$C_{2-6}$ alkyl--.

In claim 3, column 52, lines 23-24, "$C_{6-10}$heterotricycloalkyl-$C_{1-2}$-alkyl" should read --$C_{6-10}$-heterotricycloalkyl-$C_{1-2}$-alkyl--.

In claim 3, column 52, line 56, after "halogen", insert --;--.

In claim 4, column 53, line 3, "at least substituent" should read --at least one substituent--.

In claim 4, column 54, line 13, "$R_5$ is chosen" should read --$R_8$ is chosen--.

Signed and Sealed this
Fifteenth Day of September, 2015

Michelle K. Lee
*Director of the United States Patent and Trademark Office*